(12) United States Patent
MacMahon et al.

(10) Patent No.: US 11,399,941 B2
(45) Date of Patent: Aug. 2, 2022

(54) MANUALLY ADJUSTABLE DEVICE

(71) Applicant: Mitre Medical Corp., Morgan Hill, CA (US)

(72) Inventors: John MacMahon, Exeter, NH (US); Evan Anderson, Woodside, CA (US); Jeremy Boyette, Menlo Park, CA (US)

(73) Assignee: Mitre Medical Corp., Morgan Hill, CA (US)

( * ) Notice: Subject to any disclaimer, the term of this patent is extended or adjusted under 35 U.S.C. 154(b) by 491 days.

(21) Appl. No.: 16/258,519

(22) Filed: Jan. 25, 2019

(65) Prior Publication Data

US 2019/0231527 A1 Aug. 1, 2019

Related U.S. Application Data

(60) Provisional application No. 62/622,827, filed on Jan. 27, 2018, provisional application No. 62/622,830, (Continued)

(51) Int. Cl.
*A61F 2/24* (2006.01)
*A61B 17/10* (2006.01)
(Continued)

(52) U.S. Cl.
CPC .......... *A61F 2/2481* (2013.01); *A61B 17/068* (2013.01); *A61B 17/10* (2013.01);
(Continued)

(58) Field of Classification Search
CPC .... A61F 2/2446; A61F 2/2478; A61F 2/2481; A61F 2/2442; A61F 2/2445;
(Continued)

(56) References Cited

U.S. PATENT DOCUMENTS 4,042,979 A 8/1977 Angell
6,908,482 B2 6/2005 McCarthy et al.
(Continued)

FOREIGN PATENT DOCUMENTS

WO 2004043265 5/2004

OTHER PUBLICATIONS

Grayburn et al., "Proportionate and Disproportionate Functional Mitral Regurgitation", JACC Cardiovascular Imaging, 2018, pp. 1-10.
(Continued)

*Primary Examiner* — Carrie R Dorna
(74) *Attorney, Agent, or Firm* — Law Office of Alan W. Cannon

(57) ABSTRACT

Devices, systems and methods for altering functioning of a tissue/organ by application of force thereto. In one preferred embodiment, a device for reducing or preventing regurgitation of blood through a valve of a heart is provided. A device may include a main body having a segment adapted to apply force to a surface of tissue/organ; a member that applies counterforce to the force applied by the segment; and an adjuster that is manually operable to change the force applied by the segment. The adjuster can be manually operated before or after anchoring of the device to the tissue/organ.

29 Claims, 17 Drawing Sheets

Related U.S. Application Data filed on Jan. 27, 2018, provisional application No. 62/622,831, filed on Jan. 27, 2018.

(51) Int. Cl.
| | |
|---|---|
| *A61B 90/00* | (2016.01) |
| *A61B 17/068* | (2006.01) |
| *A61B 17/00* | (2006.01) |
| *A61B 17/28* | (2006.01) |
| *A61B 17/064* | (2006.01) |

(52) U.S. Cl.
CPC .............. *A61B 90/06* (2016.02); *A61F 2/246* (2013.01); *A61F 2/2442* (2013.01); *A61F 2/2451* (2013.01); *A61F 2/2466* (2013.01); *A61F 2/2478* (2013.01); *A61B 17/064* (2013.01); *A61B 17/2812* (2013.01); *A61B 2017/00243* (2013.01); *A61B 2017/00398* (2013.01); *A61B 2017/00407* (2013.01); *A61B 2017/00473* (2013.01); *A61B 2017/00738* (2013.01); *A61B 2017/00858* (2013.01); *A61B 2017/0649* (2013.01); *A61B 2090/061* (2016.02); *A61B 2090/0801* (2016.02); *A61F 2002/2484* (2013.01); *A61F 2210/0033* (2013.01); *A61F 2210/0076* (2013.01); *A61F 2220/0016* (2013.01); *A61F 2220/0025* (2013.01); *A61F 2220/0033* (2013.01); *A61F 2220/0083* (2013.01); *A61F 2230/0013* (2013.01); *A61F 2230/0023* (2013.01); *A61F 2250/001* (2013.01); *A61F 2250/0002* (2013.01); *A61F 2250/0003* (2013.01); *A61F 2250/0004* (2013.01); *A61F 2250/006* (2013.01); *A61F 2250/0007* (2013.01); *A61F 2250/0029* (2013.01); *A61F 2250/0036* (2013.01); *A61F 2250/0064* (2013.01)

(58) Field of Classification Search
CPC .... A61F 2/2448; A61F 2/2451; A61F 2/2251; A61F 2/2278; A61F 2/2281; A61F 2/246
See application file for complete search history.

(56) References Cited

U.S. PATENT DOCUMENTS

| | | | |
|---|---|---|---|
| 7,591,826 | B2 | 9/2009 | Alferness et al. |
| 7,766,812 | B2 | 8/2010 | Schroeder et al. |
| 8,012,202 | B2 | 9/2011 | Alameddine |
| 8,262,725 | B2 | 9/2012 | Subramanian |
| 8,579,798 | B2 * | 11/2013 | Mortier ............ A61B 17/00234 600/37 |
| 8,647,254 | B2 | 2/2014 | Callas et al. |
| 8,956,407 | B2 | 2/2015 | Macoviak et al. |
| 9,566,443 | B2 | 2/2017 | de Canniere |
| 9,615,926 | B2 | 4/2017 | Lashinski et al. |
| 9,636,223 | B2 | 5/2017 | Khalil et al. |
| 9,724,194 | B2 | 8/2017 | Callas et al. |
| 9,795,481 | B2 | 10/2017 | Callas et al. |
| 2002/0111533 | A1 | 8/2002 | Melvin |
| 2004/0064014 | A1 | 4/2004 | Melvin et al. |
| 2005/0119735 | A1 | 6/2005 | Spence et al. |
| 2007/0066863 | A1 | 3/2007 | Rafiee et al. |
| 2010/0004504 | A1 | 1/2010 | Callas et al. |
| 2010/0010538 | A1 * | 1/2010 | Juravic ................ A61F 2/2481 606/228 |
| 2012/0323314 | A1 | 12/2012 | Callas et al. |
| 2013/0030522 | A1 | 1/2013 | Rowe et al. |
| 2014/0172084 | A1 | 6/2014 | Callas et al. |
| 2015/0366556 | A1 | 12/2015 | Khairkhahan et al. |
| 2018/0008412 | A1 | 1/2018 | Callas et al. |

OTHER PUBLICATIONS

Kashem et al., "CardioClasp: A New Passive Device to Re-Shape Cardiac Enlargement", ASAIO Journal, 2002, pp. 1-7.

Tibayan et al., "Does septal-lateral annular cinching work for chronic ischemic mitral regurgitation?", The Journal of Thoracic and Cardiovascular Surgery, Mar. 2004, p. 654 663.

Fattouch et al., "Mitral valve therapy still surgical?", European Heart Journal Supplements, Mar. 2015, pp. A43-A48.

* cited by examiner

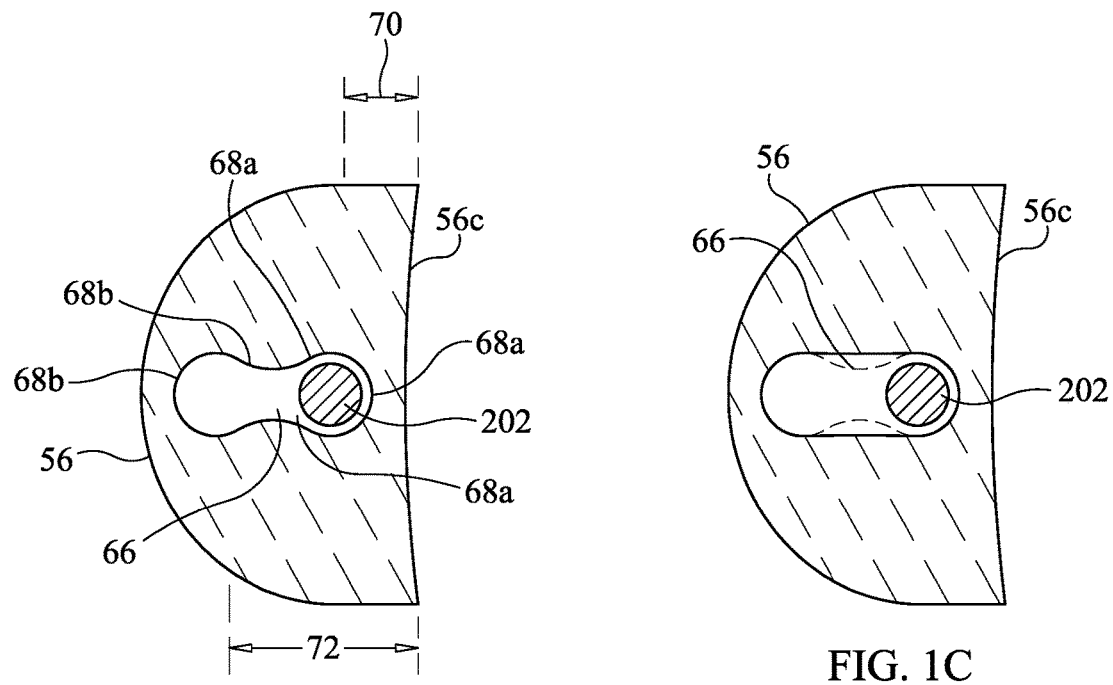
FIG. 1B
FIG. 1C
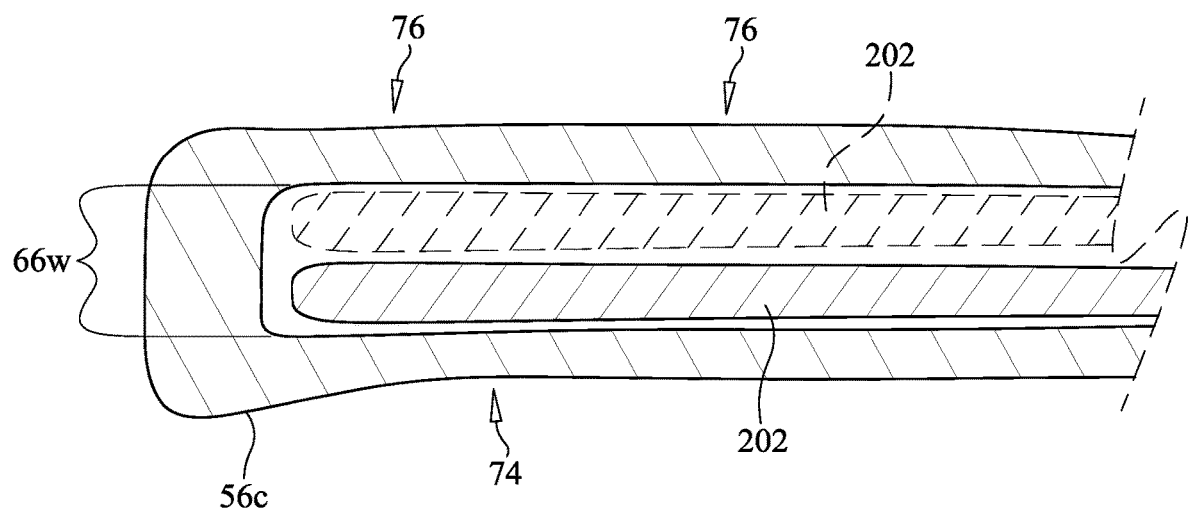
FIG. 1D

MANUALLY ADJUSTABLE DEVICE

CROSS-REFERENCE

This application claims the benefit of U.S. Provisional Application Ser. Nos. 62/622,831, filed Jan. 27, 2018; 62/622,830, filed Jan. 27, 2018; and 62/622,827, filed Jan. 27, 2018, each of which applications is hereby incorporated herein, in its entirety, by reference thereto.

INCORPORATION BY REFERENCE

All publications and patent applications mentioned in this specification are herein incorporated by reference to the same extent as if each individual publication or patent application was specifically and individually indicated to be incorporated by reference. This specification specifically incorporates US Patent Application Publication Nos. 2010/0004504 A1 and 2012/0323314 A1 herein, in their entireties, by reference thereto. Also specifically incorporated by reference in their entireties, are U.S. Provisional Application Ser. Nos. 62/622,831, 62/622,827 and 62/622,830, as noted above. Further, this specification specifically incorporates in their entireties, U.S. application Ser. No. 16/258,525, titled "Atraumatic Adjustment or Replacement of a Device for Treating Valve Regurgitation", International Application Serial No. PCT/US2019/015302, titled "Self-Adjusting Device: and International Application Serial No. PCT/US2019/015300, titled "Epicardial Valve Repair System, each of which are filed concurrently herewith.

FIELD OF THE INVENTION

The disclosure is directed to medical devices, assemblies and methods for contacting a device to tissue/organ to apply an adjustable force thereto. More particularly, the disclosure is directed to devices that are manually adjustable to adjust forces applied for reshaping the tissue/organ.

BACKGROUND OF THE INVENTION

There is broad prevalence of various organ diseases directly related to mechanical compromise of the organ tissues and/or functions. Various ones of these conditions are degenerative and progressive, for example degenerative mitral valve regurgitation. The mitral valve is located between the left atrium and the left ventricle of the heart. During normal operation, the mitral valve opens during diastole, allowing blood to flow from the left atrium into the left ventricle. During systole, the mitral valve closes, causing high pressure blood to exit the left ventricle through the aorta. Mitral valve regurgitation is a cardiac condition in which the posterior leaflet of the mitral valve does not fully contact the anterior leaflet of the valve during systole, thus a gap remains between the leaflets of the mitral valve during systole. The gap remaining between the leaflets allows retrograde blood flow to pass from the left ventricle into the left atrium through the mitral valve. Thus, mitral regurgitation reduces the volume of blood pumped out of the heart to the aorta during each cardiac cycle, thus reducing the efficiency of the heart. Mitral regurgitation may exist for any of several reasons, including congenital malformations of the valve, ischemic disease, or effects of cardiomyopathy, such as dilated (congestive) cardiomyopathy (i.e., enlarging of the heart).

Conventional techniques for treating dysfunctions of the mitral valve typically include highly invasive, open heart surgical procedures in order to replace or repair the dysfunctioning mitral valve. Some surgical procedures include the implantation of a replacement valve (e.g., animal valve or artificial mechanical valve). Other techniques include the use of annuloplasty rings which are surgically placed around the annulus of the mitral valve within the chamber of the heart and sutured into place. The presence of the annuloplasty ring alters the geometry of the annulus of the mitral valve in order to improve coaptation of the leaflets of the valve. Epicardial clips have also been proposed and used to alter the geometry of the annulus of the mitral valve. Another surgical technique which requires accessing one or more chambers of the heart is leaflet coaptation. Leaflet coaptation (e.g., Alfieri edge-to-edge repair) is a surgical procedure in which the valve leaflets are sutured together (e.g., bow-tie suture) to improve coaptation of the leaflets. A further surgical technique includes extending a tensioning cord across a chamber of the heart to alter the geometry of the heart chamber. The tensioning cord, which extends through a chamber of the heart, and thus is in contact with blood in the heart chamber, pulls opposing walls of the heart toward one another to reduce heart wall tension and/or reposition the papillary muscles within the chamber. These techniques typically require opening the heart and/or entering one or more of the chambers of the heart to gain direct access to the mitral valve.

All of the aforementioned treatments are static approaches to treatment of the disease. That is, the configuration of the devices used to treat the disease remain fixed at the time of performing the procedure. For example, implantation of a device to treat mitral valve regurgitation results in a fixed application of force and/or configuration of the device at the time that the device is implanted. If, after implanting such a device a configuration needs to be altered or force application needs to be altered, this requires a removal of the device and re-implantation of another, differently sized device or reconfigured device. Avoidance of such occurrences requires a great deal of precision with regard to the configuration/force applied by an implant device at the time of implantation. These requirements are exacerbated by procedures performed while the heart is beating.

Further, many, if not most of diseases treated, including mitral regurgitation, are degenerative, and may worsen over time. Worsening of conditions may require additional reshaping forces to be applied to maintain abatement of mitral regurgitation or other malady being treated. For example, longevity and quality of life for heart failure patients has been achieved by implantation of the MitraClip to reduce regurgitation. The clinical endpoints were cited by Grayburn et al., 2018 to parallel reduction in left ventricle volume and interesting they did not reference the reduction in regurgitation as parallel to these clinical benefits.

Therefore, it may be desirable to devise a less invasive technique for treatment of diseases such as mitral valve regurgitation and left ventricular dilation, wherein the treatment applied may be adjusted after fixation of an implant, but before closing the patient to complete the implantation procedure.

It may be further desirable to provide devices that can be adjusted after completion of a procedure by adjusting the device without having to remove it.

It may further be desirable to provide adjustable devices which maintain a desired configuration after adjustment, without concern for changing due to leakage or other factor that may cause a change in dimensional configuration of the device.

It may be desirable to devise a device, assembly and/or method useful in altering and/or reshaping the annulus of the mitral valve and/or the ventricle of a heart without the need to gain access to the interior of the heart, and which can be adjusted after fixation to the heart to alter and/or reshape the annulus and/or ventricular geometry so as to maintain satisfactory abatement or reduction of mitral regurgitation.

It may further be desirable to provide devices that can be minimally invasively implanted and/or which allow procedural reversibility and/or adjustment.

SUMMARY OF THE INVENTION

The present invention provides implantable medical devices that can be manually adjusted to adjust a force applied by a device to tissue/organ, wherein the manual adjustment can be performed even after anchoring the device to the tissue/organ. Although the devices described herein can be implanted to treat various tissues and organs, the disclosure focuses primarily on treatment of the heart, more specifically treatment of heart valve regurgitation. In at least one preferred embodiment, a device is configured to treat mitral valve regurgitation.

In one aspect of the invention; an epicardial device for reducing or preventing regurgitation of blood through a valve of a heart is provided which includes: a main body having a segment adapted to apply force to an epicardial surface of the heart; a member that applies counterforce to the force applied by the segment; and an adjuster that is manually operable to change the force applied by the segment; wherein the adjuster can be manually operated before or after anchoring of the device to the epicardial surface.

In at least one embodiment, the segment comprises a rigid structural rib contained within a pad; wherein the pad comprises a contact surface configured to apply the force to the epicardial surface; wherein the adjuster comprises a channel having stops formed therein; wherein a first set of the stops maintains the rib at a first predetermined distance from the contact surface; and wherein a second set of the stops maintains the rib at a second predetermined distance from the contact surface, the second predetermined distance being unequal to the first predetermined distance.

In at least one embodiment, the device is manually operable to change a location of the rib from being held by the first set of stops to a location where the rib is held by the second set of stops, by manually pushing against the rib, via application of pressure to the body at locations apposite the first set of stops, while applying counter-pressure to the contact surface at locations that are not apposite to the first set of stops.

In at least one embodiment, the segment comprises a first contact surface configured to apply the force as a first force to the epicardial surface; wherein the adjuster comprises a shim configured to be mounted over the first contact surface, the shim having a second contact surface; and wherein, when the shim has been mounted over the first contact surface, the second contact surface is configured to apply the force as a second force greater than the first force.

In at least one embodiment, the epicardial device is configured for reshaping an annulus of a mitral valve of the heart.

In at least one embodiment, the epicardial device is configured for reshaping an annulus of a tricuspid valve of the heart.

In at least one embodiment, the epicardial device is configured for reshaping one or more dimensions of a left ventricle of the heart.

In at least one embodiment, the epicardial device is configured for reshaping an annulus of a tricuspid valve of the heart.

In at least one embodiment, the epicardial device is configured for reshaping one or more dimensions of a right ventricle of the heart.

In at least one embodiment, the valve that the device is configured to treat is the mitral valve and the epicardial device is configured for reshaping an annulus of the mitral valve of the heart; the main body comprises an anterior segment adapted to be contacted to an anterior surface of the heart, a posterior segment adapted to be contacted to a posterior surface of the heart and a lateral segment joining the anterior segment and the posterior segment; wherein the posterior segment comprises the segment adapted to apply force and the anterior segment comprises the member that applies counterforce to the force.

In at least one embodiment, the anterior segment is configured to be positioned in the transverse sinus of the heart by ending at the right atrium; the posterior segment is configured to be positioned on or inferior to the atrioventricular groove of the heart and ending at the right ventricle; and the lateral segment extends between the anterior segment and the posterior segment.

In at least one embodiment, the posterior segment is curved to follow a contour of a posterior surface of the heart.

In at least one embodiment, the anterior segment is substantially straight.

In at least one embodiment, the member that applies counterforce comprises first and second tissue anchors, the first tissue anchor adapted to anchor a first end portion of the device to the heart and the second tissue anchor adapted to anchor a second end portion of the device to the heart, wherein the segment is located between the first and second end portions.

In at least one embodiment, the main body comprises an anterior segment adapted to be contacted to an anterior surface of the heart, a posterior segment adapted to be contacted to a posterior surface of the heart and a lateral segment joining the anterior segment and the posterior segment; wherein the posterior segment comprises the segment adapted to apply force and the anterior segment comprises the member that applies counterforce to the force.

In at least one embodiment, the device further comprises an inferior segment extending from the main body in a direction transverse to a direction in which the anterior, lateral and posterior segments extend.

In at least one embodiment, the inferior segment comprises a second segment adapted to apply a second force to an epicardial surface of the heart; wherein the inferior segment comprises a second adjuster that is manually operable to change the second force applied by the second segment; and wherein the second adjuster can be manually operated before or after anchoring of the inferior segment to the epicardial surface.

In at least one embodiment, the segment comprises a rigid structural rib contained within a pad; and the pad is covered by a sheath.

In at least one embodiment, the device further comprises a flap extending from the pad, wherein the flap is configured for receiving tissue anchors therethrough to anchor the epicardial device to the heart.

In at least one embodiment, the flap is an extension of the sheath.

In another aspect of the present invention, a method of epicardial treatment of mitral valve regurgitation associated with the mitral valve of a heart is provided, including: providing a device having an anterior segment, an anterior end, a posterior segment, a posterior end and a lateral segment extending between the anterior segment and the posterior segment; positioning the anterior and posterior segments epicardially on the heart at locations apposite to an annulus of the mitral valve, such that the anterior and posterior segments apply force sufficient to reshape the annulus; visually observing whether the mitral valve regurgitation has been successfully reduced or eliminated; and when it is observed that the mitral valve regurgitation has not been successfully reduced or eliminated, adjusting the force applied by the anterior and posterior segments by manually operating an adjuster that changes a distance between the posterior and anterior segments.

In at least one embodiment, the adjusting is performed prior to anchoring the device epicardially on the heart.

In at least one embodiment, the adjusting is performed after anchoring the device epicardially on the heart.

In at least one embodiment, the adjusting comprises applying pressure to a rib within a pad of the posterior or anterior segment, at locations apposite a first set of stops within a channel in the pad, while applying counter-pressure to a contact surface of the pad at locations that are not apposite to the first set of stops, thereby driving the rib from a first set of stops to a second set of stops; wherein the first set of stops are located at a first depth from the contact surface within the channel and the second set of stops are located at a second depth from the contact surface within the channel, the first depth being unequal to the second depth.

In at least one embodiment, the posterior segment comprises the pad.

In at least one embodiment, the adjusting comprises mounting a shim on or removing a shim from a first contact surface of a pad of the anterior or posterior segment; where the shim comprises a second contact surface; and wherein, when the shim has been mounted over the first contact surface, the second contact surface is configured to apply the force as a second force greater than the first force.

In at least one embodiment, the posterior segment comprises the pad.

In at least one embodiment, the visually observing is performed echocardiographically.

In at least one embodiment, the method further includes: prior to the positioning, applying a force to a posterior surface of the heart while visually observing blood flow through the mitral valve; varying the force to establish a force that successfully reduces or eliminates the mitral valve regurgitation; and measuring a distance between a posterior external wall and an anterior external wall of the heart in a deformed state resultant from the application of force that successfully reduces or eliminates the mitral valve regurgitation, the distance being measured between locations where the device is to be positioned; and wherein the providing a device includes selecting the device to have a distance between the anterior and posterior segments that corresponds to the distance measured.

In at least one embodiment, the positioning comprises: positioning the anterior segment in the transverse sinus of the heart; positioning the posterior segment on or inferior to the atrioventricular groove of the heart, wherein the device reshapes the annulus of the mitral valve; and wherein the anterior and posterior ends are spaced apart from one another by a predetermined distance and remain separated by a gap or opening after the positionings.

Additionally, a method of providing an initial anchor at the apical edge of the securement flap, in between the pad and said anchor includes a method of adjusting tension similar to the method of adjustable blinds where stay sutures provide for vertical and/or lateral displacement adjustability and subsequent position change or tension in the pad.

These and other features of the invention will become apparent to those persons skilled in the art for aortic, pulmonary and/or tricuspid valves, upon reading the details of the devices, systems and methods as more fully described below.

BRIEF DESCRIPTION OF THE DRAWINGS

The invention may be more completely understood in consideration of the following detailed description of various embodiments in connection with the accompanying drawings in which:

FIG. 1B is a cross-sectional view of FIG. 1A taken along line 1B-1B;

FIG. 1C is a cross-sectional view of FIG. 1A taken along line 1C-1C;

FIG. 1D is a longitudinal sectional view of the posterior segment of FIG. 1A taken in the plane of the drawing sheet.

DETAILED DESCRIPTION OF THE INVENTION

Figure 1A:
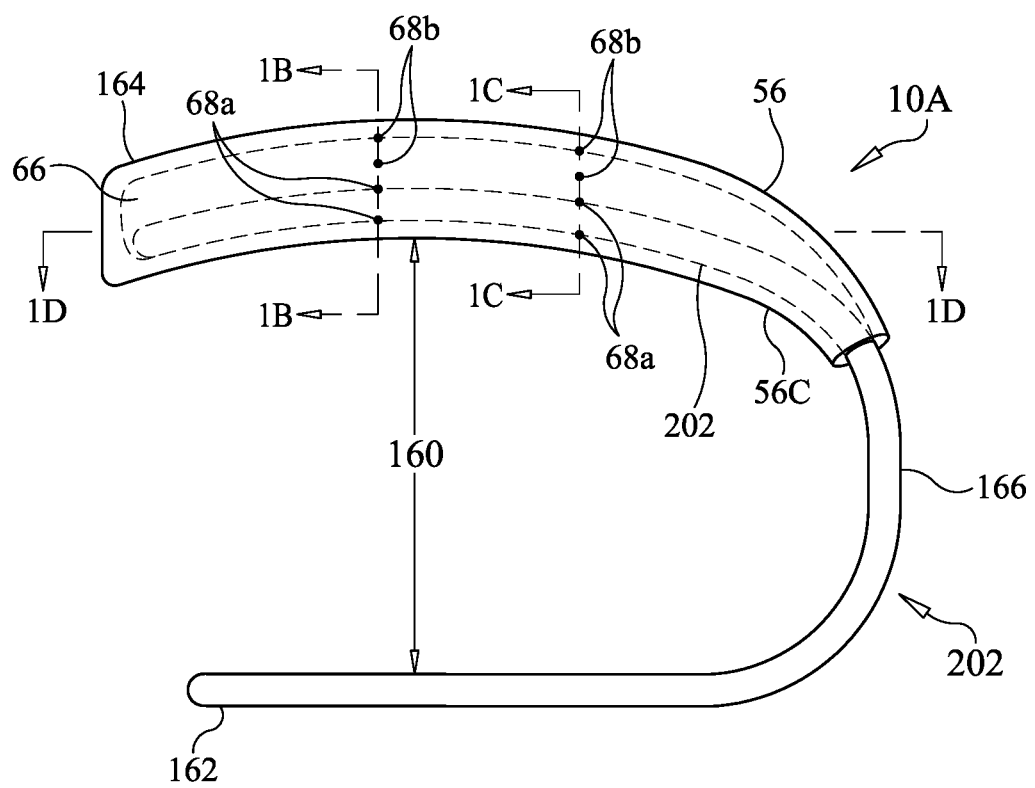
FIG. 1A illustrates an implantable device according to an embodiment of the present invention.

Before the present devices, components and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a shim" includes a plurality of such shims and reference to "the pad" includes reference to one or more pads and equivalents thereof known to those skilled in the art, and so forth.

As used in the specification and the appended claims, the term "anterior" is used in its anatomical sense to mean "toward the front, in front of, or the front surface of."

As used in the specification and the appended claims, the term "posterior" is used in its anatomical sense to mean "toward the back, in back of, or the back surface of."

As used in the specification and the appended claims, the term "superior" is used in its anatomical sense to mean "above, over top of, directed upward or toward the head."

As used in the specification and the appended claims, the term "inferior" is used in its anatomical sense to mean "below, underneath, directed downward or toward the feet."

As used in the specification and the appended claims, the term "lateral" is used in its anatomical sense to mean "a position or direction farther from the sagittal or median plane or midline of the body, to the side of, or the side surface of."

The publications discussed herein are provided solely for their disclosure prior to the filing date of the present application. Further, the dates of publication provided may be different from the actual publication dates which may need to be independently confirmed.

The manually adjustable features of the present invention can be used to fine tune an amount of force applied by an implantable device to a tissue or organ even after the device has been attached to the tissue or organ. With more specific reference to devices used to treat heart valve regurgitation, the devices of the present invention can be implanted in a configuration so as to apply force to reshape a valve annulus and/or reshape a ventricle so as to improve coaptation of heart valve leaflets to significantly reduce or eliminate valve regurgitation and to reshape the left ventricle. In some cases, after assessment of valve regurgitation to determine the conformation of a device to be implanted that successfully reduces or eliminates valve regurgitation, such as by applying force to the heart in an amount to observe such successful reduction or elimination, and recording the location where the force is applied during such observation, as well as measurements of the amount of deformation/reformation of the annulus and/or ventricle that result from the application of the force, an appropriate device and/or devices can be selected for implantation so as to apply forces and amounts of deformation epicardially to the heart to accomplish the observed successful reduction or elimination of valve regurgitation.

Epicardial devices, when implanted may apply force to both anterior and posterior (and potentially, lateral) surfaces of the heart to translate these forces for the desired reshaping of the annulus and/or ventricle. In order to apply manual force to the heart during the observation stage described above, this will typically require lifting the heart (when the patient is in a supine position) to allow application of force to the posterior surface of the heart. This poses potential problems, as it is often difficult to observe the exact location or footprint of the application of force to the posterior surface. Even when an accurate observation of the footprint can be made, it still may be difficult to accurately locate the posterior portion of the device on the footprint, as it is difficult, if not impossible to directly visualize the placement of the device relative to the posterior surface. Other potential problems include those where the distance between the anterior and posterior portions of the device are separated by a distance that is not sufficient to apply the exact amount of force (or near enough to exact to establish the successful result) needed to repeat the successful outcome observed during the observation stage prior to implantation.

Implantation of such devices often includes anchoring the device against the heart surface with tissue anchors that extend into the myocardium, for example. In occurrences such as noted above, the present invention allows manual adjustment of the force applied by a device against the heart tissue so as to improve results for reducing or eliminating valve regurgitation. Such adjustment can be performed even after anchoring the device epicardially to the heart, thereby eliminating the need to remove and implant and reinstall it with a different or reconfigured implant. This also eliminates the need to remove tissue anchors in an effort to reshape the implant if such occasions occur where this is possible. Still further, the present invention allows procedures, after completion of implantation, to reenter the target site to manually adjust the device to change the force applied thereby, in situations, such as degenerative complications, where additional force may be needed to be applied at some time after the initial implantation, to restore the successful reduction or elimination of valve regurgitation. With these procedures, it is not necessary to remove the device or even to remove the tissue anchors.

FIG. 1 is a top view of an epicardially implantable device 10A according to an embodiment of the present invention. In this embodiment, device 10A may have a generally U-shape or C-shape when viewed with this orientation. The device 10A may be shaped such that the distance 160 across the device 10A between the contact surface of the anterior segment 162 and the contact surface of the posterior segment 164 defines the space between which the mitral valve and mitral valve annulus (as well as the heart walls apposite these features) will be located after implantation of the device 10A and may determine the final anterior-posterior diameter of the mitral valve annulus. The anterior segment 162 may be substantially straight, and thus capable of residing in the transverse sinus of the heart. The posterior segment 164 may be arcuate, corresponding to the convex curvature of the posterior ventricular wall of the heart in a location where it is designed to be positioned for implantation. The lateral segment 166 interconnects the anterior 162 and posterior 164 segments with a sufficient length to establish the appropriate distance 160 between the segments 162 and 164 for effectively applying force to the mitral valve annulus to cause a reduction or elimination of mitral valve regurgitation. The main body or frame 202 of device 10A is non-flexible and is rigid to an extent wherein the conformation shown is not readily deformed and is not deformed by the forces applied to it by the beating heart when it is implanted. In this embodiment, frame 202 is formed by a metal wire, preferably out of titanium or titanium alloy, but could alternatively be formed from other biocompatible metals such as stainless steel, such as 304V, 304, and 316LV stainless steel; mild steel; nickel-titanium alloy such as linear-elastic and/or super-elastic nitinol; other nickel alloys such as nickel-chromium-molybdenum alloys, and the like.

The posterior segment 164 in this embodiment includes a pad 56 which is preferably compliant and is atraumatic when contacted to target tissue such as the heart. Pad 56 encases at least a portion of, preferably substantially all of the posterior segment portion 164 of the frame (rod) 220. Pad 56 is preferably made from silicone, but could alternatively be made from other moldable, biocompatible polymers.

The lengths and orientations of the anterior 162, posterior 164 and lateral 166 segments may include any of those described in US Patent Application Publication No. 2012/0323314 which is hereby incorporated herein, in its entirety, by reference thereto. Device 10A may be configured so that the lateral segment 166 can be routed around the left lateral side of the heart, placing the anterior segment 162 in the transverse sinus and the posterior segment 164 on the posterior of the heart, such as on or inferior to the atrioventricular groove or in the oblique sinus of the heart. In some embodiments the lateral segment 166 may be routed around, over and/or under the left atrial appendage of the heart. In other embodiments, the lateral segment 166 may be routed over the left atrium of the heart.

In some variants of this and all other embodiments described herein, the device may include a drug eluting coating in addition to pad 56. The drug eluting coating may be provided in addition to a sheath or as an alternative to the sheath. The drug eluting coating may a controlled release of a therapeutic agent over a specified period of time. The therapeutic agent may be any medicinal agent which may provide a desired effect. Suitable therapeutic agents include drugs, genetic materials, and biological materials. Some suitable therapeutic agents which may be loaded in the drug eluting coating include, but are not necessarily limited to, antibiotics, antimicrobials, antioxidants, anti-arrhythmics, cell growth factors, immunosuppressants such as tacrolimus, everolimus, and rapamycin (sirolimus), therapeutic antibodies, wound healing agents, therapeutic gene transfer constructs, peptides, proteins, extracellular matrix components, steroidal and non-steroidal anti-inflammatory agents, antiproliferative agents such as steroids, vitamins and restenosis inhibiting drugs, such as TAXOL®, paclitaxel (i.e., paclitaxel, paclitaxel analogues, or paclitaxel derivatives, and mixtures thereof).

Pad 56 includes a contact surface 56C that is configured to contact a posterior surface of the heart when implanted, according to this embodiment. The contact surface 56C is preferably curved to follow a contour of a posterior surface of the heart at a location where it is designed to be implanted. All corners and ends of the pad are rounded or otherwise structured so as to be atraumatic to surrounding tissues during and after implantation of the device 10A.

Implantation of the device 10A may be secured by tissue anchors 54, such as those illustrated in FIG. 4A or many other equivalents, installed through the pad 56, a sheath 57 encasing the pad 56 or a flap 85 extending from the pad, sheath or elsewhere on the device 10A (or other embodiment of device 10) and into the epicardium and/or myocardium, as described in further detail with regard to FIGS. 5 and 6 below.

The posterior section of rod 202 forms a structural rib that is encased by pad 56 and is retained within a channel 66 formed within pad 56. Channel 66 has sufficient length, width and depth to allow rib/rod portion 202 to slide freely between at least two different predefined locations along the width 66W (see FIG. 1C) of the channel. Stops or restrictions 68 (68a, 68h, and potentially more) are formed in the pad to reduce the depth of the channel 66 at predefined locations so as to maintain the rib 202 in one of a plurality of predefined locations. For example, the embodiment of FIG. 1A has two sets of stops/restrictions 68a and 68b and FIG. 1A illustrates the rib 202 (in phantom lines) being retained by stops 68a. However, the present invention is not limited to two sets of stops/restrictions, as three or more sets could be provided in the pad 56. Likewise, although each set 68a, 68b is shown to be provided at only two locations along the length of the channel 66, three or more locations (or even only one location) could be provided for each set.

FIG. 1B is a cross-sectional illustration of the posterior segment of the device of FIG. 1A taken along line 1B-1B, along the location where some of the stops/restrictions are located (i.e., the leftmost restrictions 68a, 68b of FIG. 1A). FIG. 1C is a cross-sectional illustration of the posterior segment of the device taken along line 1C-1C, along a section where no restrictions/stops are located. Thus, FIG. 1C-1C illustrates the full depth/thickness of the channel 66 and shows the restricted depth/thickness of the next set of stops (in phantom) further along the length of the channel. As shown in solid lines in FIG. 1B, the restrictions/stops 68a, 68b reduce the depth (thickness) of the channel 66 to a depth/thickness that is sufficiently less that the diameter of the rod/rib 202 to retain it between the stops 68a or 68h, wherein a force required to move the rod/rib from a location captured by stops 68a to a location captured by stops 68b or vice versa is greater than a force that will be applied by the contact surface 56C of the pad 56 against the wall of the heart when the device 10A is in use. However, the force required to move the rod/rib from one predefined location (e.g., 68a or 68b) to another predefined location (e.g., 68b or 68a, respectively) is one that can be readily exceeded by manual application of forces by a surgeon or other person involved in installation of the device 10A.

As shown in FIG. 1B, rod/rib 202 is retained in the predefined position defined by stops 68a. In this position, the rod/rib 202 is maintained substantially parallel or following the contours of contact surface 56C so that it can maintain relatively even structural support/application of force through the contact surface 56C to the surface of the heart lengthwise along the contact surface.

The rod/rib 202 is maintained at a first predefined distance 70 from the contact surface 56C measured normally thereto. Application of pressure/force to the pad 56 in amounts greater than those that can be applied through contact with the beating heart and which are great enough to overcome the restrictive forces from the stops on the rod/rib can cause the rod/rib 202 to be repositioned from one predefined location defined by a first set of stops to a second predefined location defined by a second set of stops. For example, application of force 74 to the contact surface 56C at a location apposite stops 68a and simultaneous application of force 76 to the opposite surface of the pad 56 at one or more locations adjacent to the location apposite the same stops 68a, wherein the combined forces 74 and 76 are sufficient to overcome the resistance of the stops 68a to movement of rod/rib 202 through the channel 66, causes the rod/rib 202 to move from the predefined location where it is retained by stops 68a (shown in solid lines in FIG. 1D) to the predefined location where it is retained by stops 68b (shown in phantom lines in FIG. 1D).

This process can be repeated at each location along the length of the pad 56 where stops are located. Upon completion of this process, rod/rib 202 will be located at the predefined distance 72 (see FIG. 1B) from and normal to the contact surface 56C. It is noted that this process is also reversible to move the rod/rib 202 from the location defined by stops 68b to the location defined by stops 68a. It is further noted that the location of force 76 can be applied apposite to the stops on the surface opposite the contact surface 56C, with one or more forces 74 being applied to the contact surface 56C at locations adjacent to the location apposite the stops to achieve the same results. In other embodiments, three or more sets of stops may be provided in channel 66. In an embodiment where three sets of stops are provided, the rod/rib 202 could be initially positioned in an intermediate predefined position, so that it could be thereafter manually moved to a predefined position closer to the contact surface 56 or to another predefined position further away from the contact surface and measured normal thereto, relative to the normal distance of the intermediate position from the contact surface 56. The predefined distance 70 may be any distance down to half the diameter of the rod 202 and may be in a range of 0 to 1 mm plus half the diameter of the rod 202, 1 to 2 mm plus half the diameter of the rod 202, 2 to 4 mm plus half the diameter of the rod 202, or any value within these ranges. The predefined distance 72 may be any distance from a range of distance 70 plus the diameter of the rod to distance 70 plus the diameter of the rod plus 1 mm, plus 2 mm or plus 4 mm, or any values therebetween. In one non-limiting embodiment, movement of rod 202 from 68a to 68b changes this distance between the center of the rod/rib 202 and the contact surface 56c by 1 mm. In another embodiment the change is 2 mm. However these values may vary as desired.

Thus, in the embodiment shown in FIG. 1A-1D, manual adjustment of the device 10A as described above to move rod/rib 202 from a predefined position where it is retained by stops 68a to a second predefined position where it is retained by stops 68b would result in the contact surface 56C applying relatively greater force to and displacement of the heart tissue and thereby a larger change in the reshaping of the mitral annulus, since, as noted, the frame 202 will remain in its constant predefined orientation and will not deform. Such an adjustment can be used to successfully reduce or eliminate mitral valve regurgitation.

For example, in some instances an observation of a successful reduction or elimination of mitral regurgitation can be obtained while a surgeon applies force to a posterior wall of the heart prior to implantation of the device. The amount of deformation caused by the successfully applied amount of force can be measured from recordations of the observation, such as echocardiograms and an appropriate device 10A can be selected for implantation to achieve the measured amount of deformation when the device is implanted.

However, there are many factors that must be taken into account to repeat the deformation in the manner in which it was achieved during the initial observation, including, but not limited to the distance between the anterior 162 and posterior 164 segments of the device, and the location placement of the anterior 162, lateral 166 and posterior 164 segments epicardially against the heart walls. Because it is typically impossible to see the location of the posterior segment 164 as it is placed, there is potential for the posterior segment 164 (as well as other segments 162, 166, but particularly the posterior segment) to be slightly mispositioned, relative to the location that was originally identified. When this occurs, there is potential for the implanted device to reduce mitral valve regurgitation significantly from what it was untreated, but not to the extent that was observed echocardiographically when the surgeon manually applied deformation to the posterior wall of the heart, prior to implantation of the device 10A. In such instances, it may be possible to leave the device 10A in its implanted position and manually adjust the pad 56C and rod 202 so that rod 202 is moved from 68a to 68b as described in the example above. After this manual adjustment, re-observation (or continued observation) of the blood flow through the mitral valve may show a reduction (relative to the amount of regurgitation observed initially after implanting the device 10A, but prior to the manual adjustment) or elimination of mitral valve regurgitation.

It is further noted that the manual adjustment of the pad 56C relative to the rod 202 can be performed prior to, or even after anchoring the device 10A using tissue anchors 54. For example, the surgeon can insert one or more fingers between the contact surface 56 and the posterior wall of the heart to apply force 74 and use one or more thumbs or fingers to apply counterforce 76 to the opposing surface of the pad 56 to achieve the manual adjustment in a manner as described above.

Figure 2A:
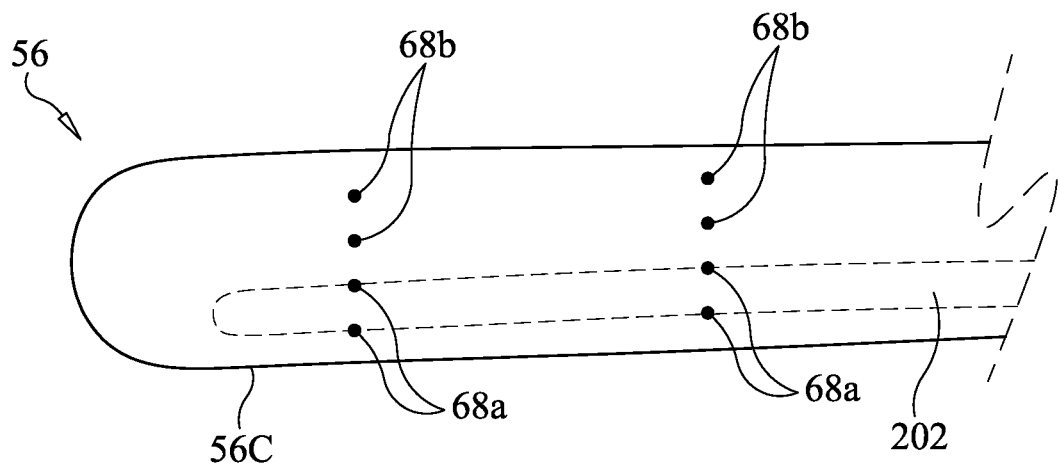
FIG. 2A illustrates a rod/rib being retained in a predefined position by stops according to an embodiment of the present invention.
Figure 2B:
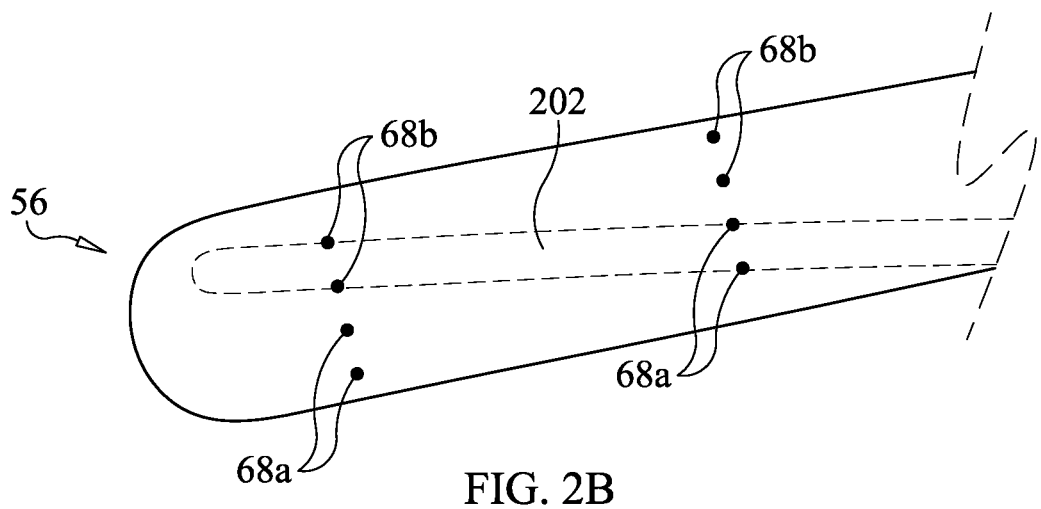
FIG. 2B illustrates results of a manual adjustment of the rod/rib of FIG. 2A relative to the pad.

Although the description of FIGS. 1A-1D above refers to predefined positions wherein the rod/rib 202 is maintained substantially parallel or following the contours of contact surface 56C so that it can maintain relatively even structural support/application of force through the contact surface 56C to the surface of the heart lengthwise along the contact surface, it is noted that the present invention is not limited thereto, as the rod/rib 202 can be retained in predefined positions wherein the force profile along the length of the contact surface 56C can be altered by manually adjusting the rod/rib 202 relative to the pad 56. FIG. 2A illustrates rod 202 being retained in a predefined position by stops 68a, like that shown in FIG. 1D and described above. By applying forces as described above to the pad 56 only around the location of the first (leftmost in FIG. 2A) group of stops 68a, a manual adjustment can be made whereby rod/rib 202 resides in a predefined position wherein the left portion of the rod 202 (near the free end) is located further from the contact surface (measured normal thereto) then is the right portion of the rod 202, as shown in FIG. 2B, as the left portion is retained by stops 68b and the right portion remains retained by stops 68a. In this instance a greater force/displacement of the tissue contacted by the contact surface nearer the free end of the pad 56 would result, relative to the force displacement of the tissue contacted by the contact surface in a region nearer to the lateral portion 166.

Figure 3A:
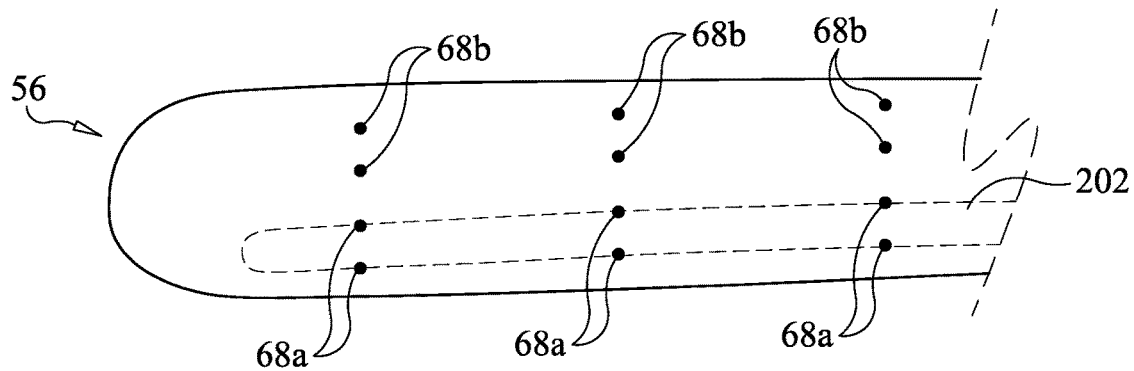
FIG. 3A illustrates a rod/rib being retained in a predefined position by stops according to another embodiment of the present invention.
Figure 3B:
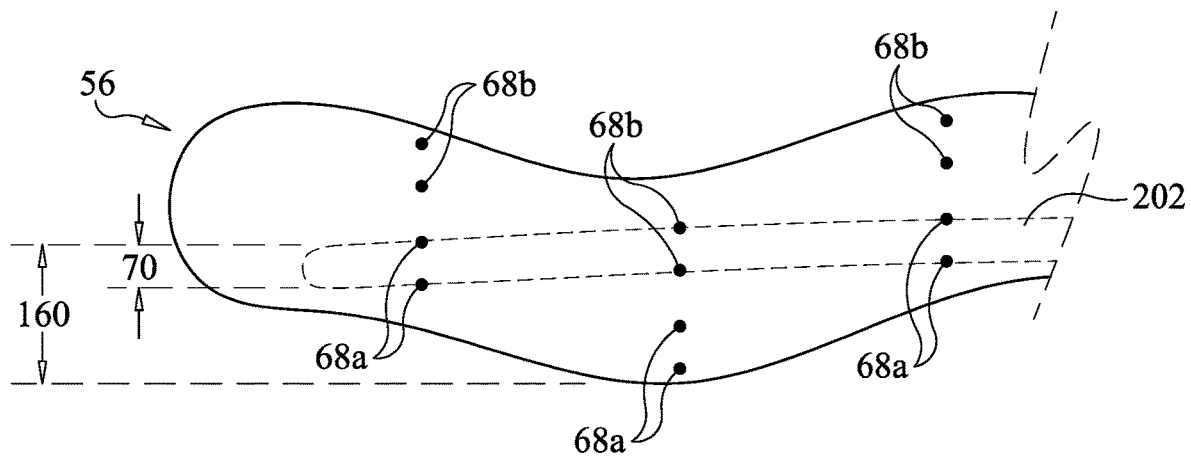
FIG. 3B illustrates results of a manual adjustment of the rod/rib of FIG. 3A relative to the pad.

FIG. 3A illustrates three groups of stops per set of stops 68a, 68b, with rod/rib 202 retained by stops 68a. This illustration demonstrates a further capability of adjusting the rib 202/pad 56, so that, after adjustment, rod/rib 202 is still retained by stops 68a at both end portions while the intermediate portion of rib/rod 202 has been moved to be retained by stops 68b of the intermediate group of stops. This results in the conformation of the contact surface 56c changing as shown so that the intermediate portion of the contact surface 56c at a location apposite to the intermediate stops 68b extends by a normal distance 72 from rib 202 that is greater than the normal distance 70 from rib 202 which the contact surface 56c at locations apposite the rib 202 where retained by the left and right end stops 68a, as illustrated in FIG. 3B. because the pad is pliable, the contact surface 56c bends so that it is convexly curved between locations apposite the end stops and thus has a greater normal distance to the rod/rib 202 at all points located between points apposite to the end stops. FIGS. 2A-3B are provided only as examples of that types of adjustability that can be made available by the provision of this embodiment. For example, the contact surface 56c could be made to be concave through adjustments that would be readily apparent to one of ordinary skill in the art after reading the above description. Further alternatively, the contact surface 56c could be made serpentine (with at least 4 groups of stops per set of stops), ramped, or the like. This flexibility in adjustment allows not only the amount of force and displacement applied by the device 10A to be increased or decreased, but further allows the contour of the force application by contact surface 56c to be varied. For example, a distal portion of the contact surface could be altered to increase application of force/displacement while the proximal portion of the contact surface is unchanged (FIG. 2B), etc.

Figure 4A:
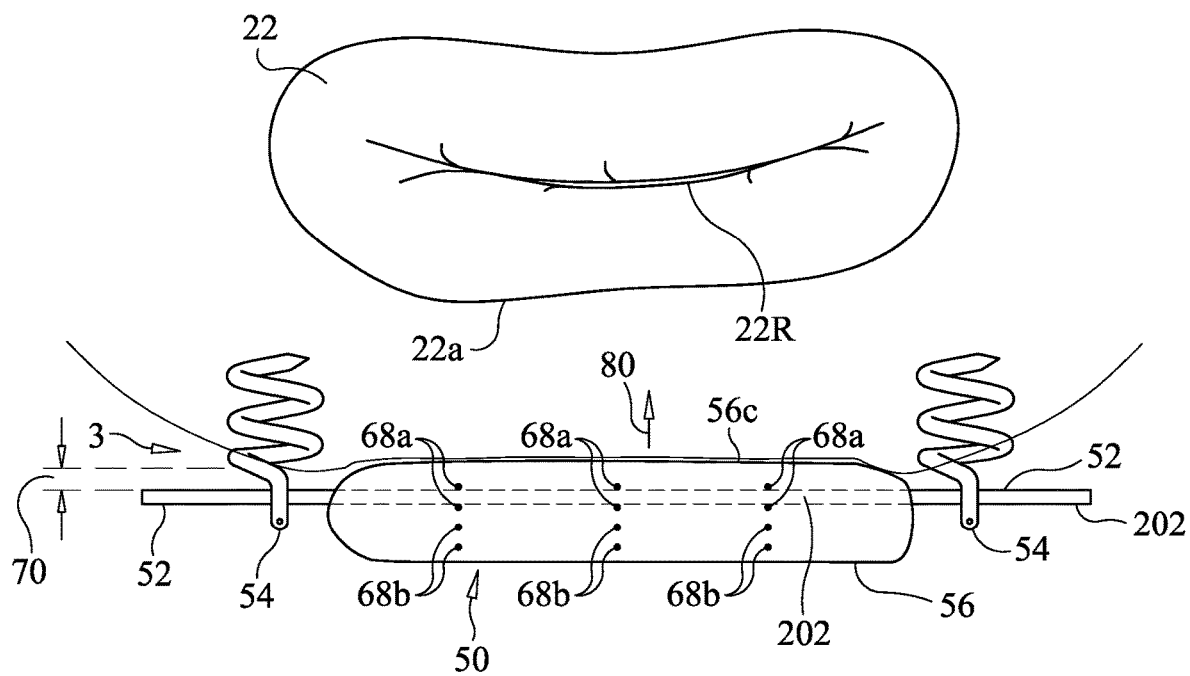
FIG. 4A illustrates an implantable device anchored epicardially to a heart according to another embodiment of the present invention.
Figure 4B:
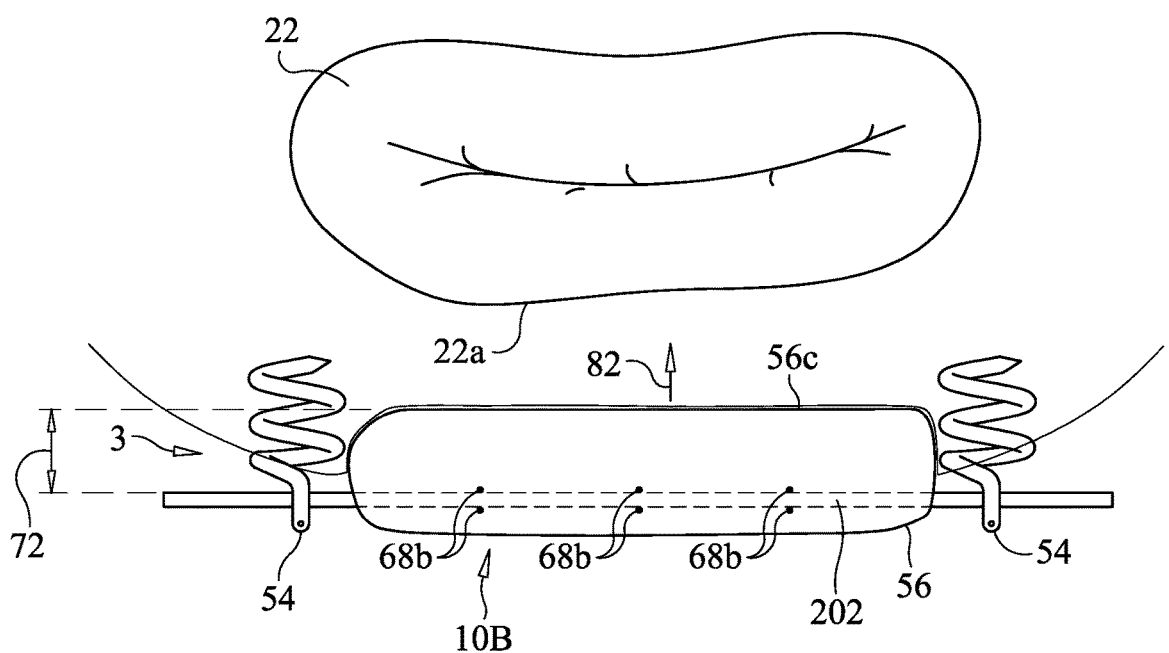
FIG. 4B illustrates the implantable device of FIG. 4A after manual adjustment thereof.

FIGS. 4A-4B illustrates a device 10B having manual adjustment features like those of device 10A according to another embodiment of the present invention. The same reference numeral scheme is applied throughout for features that are comparable between different embodiments. Device 10B is configured to be anchored to tissue/organ of a patient so as to be operable to apply forces thereto to modify the functioning of the tissue/organ. For example, FIG. 4A illustrates device 10B installed epicardially on the heart 3 of a patient for treatment of mitral valve regurgitation as one of the preferred embodiments of location of implantation. In this preferred embodiment, device 10B can be installed epicardially on the heart 3 over a target location to effect reshaping of the mitral valve annulus 22a. The device 10B may be anchored to the wall of the heart at the level of the mitral valve 22 via tissue anchors 54 as described. In another use, device 10B can be configured to be installed epicardially on the heart to apply forces thereto to improve tricuspid valve functioning. In another use, device 10B can be configured to be installed epicardially on the heart to apply forces thereto to reduce tension on chordae tendineae to improve functioning of a heart valve.

Rod/rib 202 extends through the main body 50 of device 10B and forms extension rods 52 that extend from both ends of main body 50. Rod/rib 202 is preferably substantially straight as shown, but could alternatively include one or more curves. The main body is formed by pad 56 which surrounds or encases the portion of the rod/rib extending therethrough.

Extension rods 52 can be configured to engage with tissue anchors 54. Tissue anchors 54 may be selected from many variable types, including, but not limited to, any of those disclosed in US Patent Application Publication No. 2010/0010538 published on Jan. 14, 2010, which is hereby incorporated herein, in its entirety. As noted above, rod/rib 202 (which includes extension rods 52) is rigid. By rigid, what is meant is that the rod/rib 202 has sufficient rigidity to maintain its shape without deformation under normal operating conditions. Thus, application of a typical external force on the rod/rib 202, such as forces applied by the beating heart in embodiments installed on the heart, will not appreciably alter the shape thereof. For example, in some embodiments an external force of 5 Newtons or less, 10 Newtons or less, 15 Newtons or less, 20 Newtons or less, or 25 Newtons or less applied to the rod/rib 202 would not result in appreciable deflection, deformation or bending thereof. Furthermore, the rod/rib 202, unlike a cord or cable, may be capable of withstanding axially compressive forces without collapsing and/or may be capable of withstanding bending forces without deflection. In some embodiments, the rod/rib 202 may have a modulus of rigidity (bending and/or compression) of greater than 25 GPa, greater than 30 GPa, greater than 40 GPa, greater than 50 GPa, greater than 60 GPa, greater than 70 GPa, or greater than 80 GPa.

In some embodiments, the rod/rib 202 and contact surface 56c may be straight or substantially straight, or in other embodiments, the rod 202 and contact surface 56c may be curved or bent into a desired shape and the extension rod portions 52 of the rod 202 may be curved or straight. In some embodiments the contact surface 56c and rod 202 may have a curvature approximating the curvature of the external curvature of a wall of a heart. In some embodiments, the extension shafts 52 may be eliminated altogether, such that the main body 50 extends over the lengths occupied by the extension shafts 52 in FIG. 4A.

In FIG. 4A, the rod/rib 202 is shown captured by the stops 68a, such that the normal distance measurement between rod/rib 202 is 70 and a force 80 applied to the external wall of the heart 3 results in a deformation of the heart wall and annulus 22a of the mitral valve 22 as shown. For exemplary purposes, FIG. 4A illustrates that the valve leaflets of the mitral valve have not been completely closed by this reshaping of the mitral valve annulus 22a, where a small separation 22R remains between the leaflets to allow some mitral valve regurgitation.

FIG. 4B illustrates the implanted device 10B of FIG. 4A, after manual adjustment of the device to move rod/rib 202 relative to pad 56 so that rod/rib 202 is captured by stops 68b. After this adjustment the normal distance measurement between rod/rib 202 is 72 and this greater distance (relative to distance 70) results in application of a force 82 that is greater than force 80 applied to the external wall of the heart 3, therefore resulting in greater deformation of the heart wall and annulus 22a of the mitral valve. As shown in FIG. 4B this greater deformation/reshaping of the annulus 22a has resulted in the complete closing of the valve leaflets of the mitral valve 22 so that mitral valve regurgitation no longer occurs.

Figure 5:
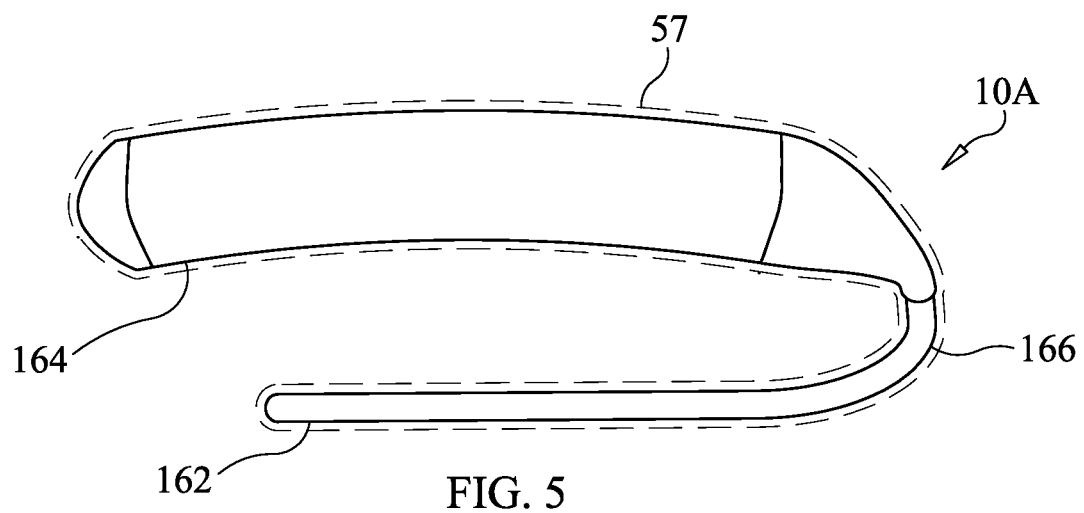
FIG. 5 illustrates an implantable device encased with a sheath according to an embodiment of the present invention.
Figure 6:
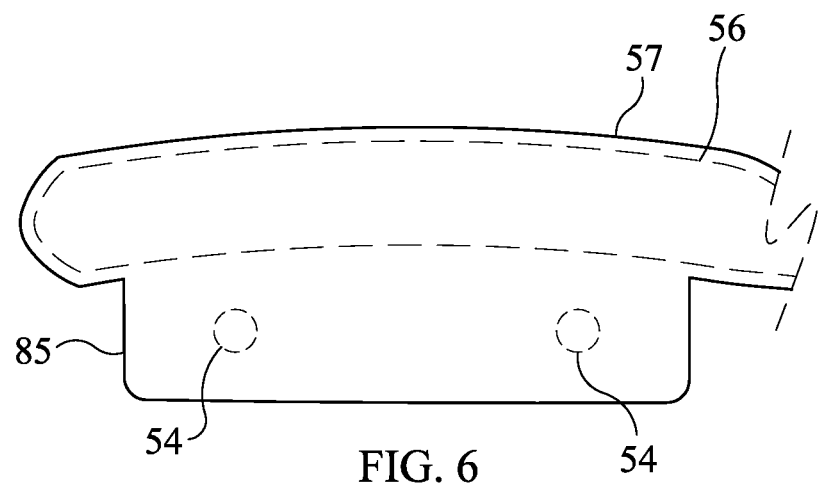
FIG. 6 illustrates a posterior segment of an implantable device having a flap extending therefrom, according to an embodiment of the present invention.

FIG. 5 illustrates that a device 10 of the present invention may include or be wrapped in a sheath 57 in some embodiments of the present invention. Although FIG. 5 shows device 10A as an example, any of the embodiments of device 10 of the present invention may include a sheath 57. The sheath may cover all or only a portion of the device. For example, FIG. 5 shows sheath 57 encasing the entire device 10A. Alternatively, sheath 57 may only cover the posterior segment 164, or the posterior 164 and lateral segments 166, or the anterior 162 and posterior 164 segments, or any desired portion of the device 10A, 10B or 10.

The sheath 57 may comprise an expanded polytetrafluoroethylene (ePTFE) material, a polyester knitted fabric, a polyester velour, a polypropylene felt, a woven or braided fabric, a non-woven fabric, porous material, or other textile material that is biocompatible. Further material choices for pad 56 and/or sheath 57 can be any of those described with regard to pad 58 in US Patent Application Publication No. 2010/0010538. The pad 56, which may be at least partially formed of a compliant material, may more evenly distribute stresses from the rod 202 to the surface of the tissue/organ, prevent lateral motion of the device 10 positioned on the tissue/organ, and/or provide an area for securing the device 20 to the tissue/organ. In some embodiments the pad 56 may distribute clamping forces to avoid occluding arteries and/or veins on the myocardium and/or epicardium or other tissue to which device 10 is attached. In some embodiments the pad 56 may provide sufficient torsional flexibility, allowing the device 10 to conform to the contours of the heart or other tissue/organ to which it is attached. When a sheath 57 is employed, sheath 57 may promote tissue in-growth into interstices of the sheath, and/or provide adequate frictional forces to hold the device 10 in contact with the heart and prevent migration of the device 10 once positioned on the heart.

In some embodiments a flap may be provided to extend from a portion of the device 10 to facilitate anchoring the device 10 to tissue/organ. FIG. 6 illustrates a flap 85 that extends from sheath 57 on the posterior segment 164 of a device 10A. In this embodiment, flap 85 is made of the same material as sheath 57. Alternatively, flap 85 can be made of the same or different material a sheath 57 or pad 56 and may extend from pad 56 or from rod 202. As illustrated in FIG. 6, tissue anchors 54 are shown in phantom lines indicating that tissue anchors 54 may be applied through flap 85 for attachment into the underlying tissue/organ. Although two tissue anchors 54 are shown, one or three or more tissue anchors 54 may be alternatively used. In the case where device 10A is installed to treat mitral valve regurgitation, tissue anchors 54 may be installed through flap 85 and into heart wall tissue on a posterior wall of the heart to anchor the device 10A in position. As noted previously, a device 10 can be adjusted before or after such anchoring, and this applies to all embodiments of devices 10 and manual adjustment described herein.

Figure 7A:
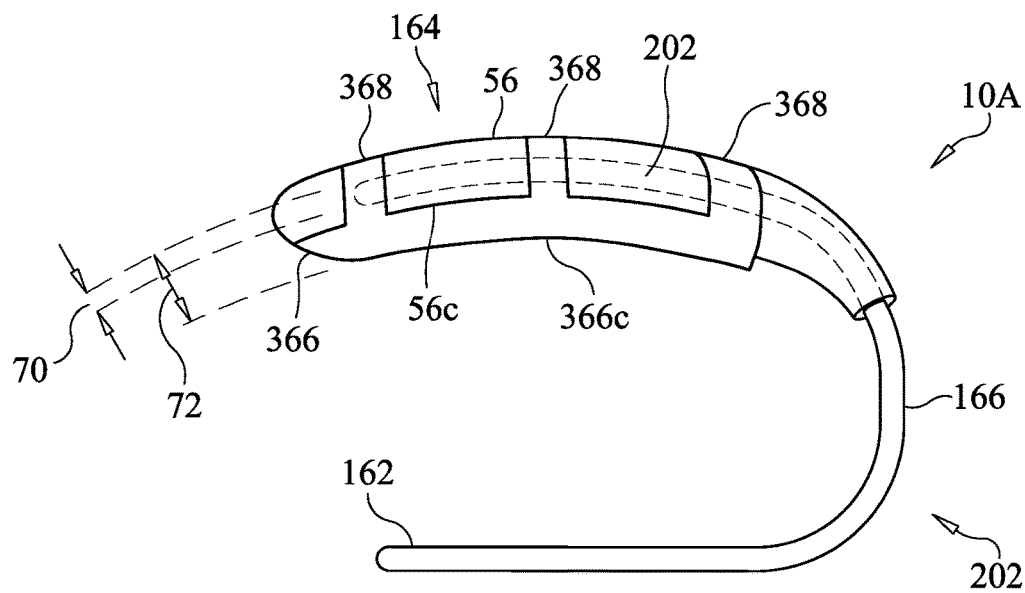
FIG. 7A illustrates an implantable device according to another embodiment of the present invention.

FIG. 7A illustrates a device 10A employing a shim 366 as a manual adjustment feature according to an embodiment of the present invention. The normal distance 70 between rod/rib 202 and a surface that contacts tissue/organ can be increased by attaching shim 366 over the contact surface 56c of pad 56 as shown. In this way, the distance 70 between rod/rib 202 and contact surface 56c of the pad 56 is increased to distance 72 between the rod/rib 202 and the contact surface 366c of the shim 366.

Shim 366 is preferably made of the same material as pad 56, but could be a different material, and is preferably pliable and compliant. The shim 366 when installed, preferably covers most or all of the contact surface 56c but could cover only a portion thereof. Contact surface 366c may cover 100%, 95%, 80%, 75%, 60%, 50%, 40%, 30%, 20% or less of the area of contact surface 56c, or any value therebetween. Shim 366 may include extensions 368 (shown in FIG. 7a, but better shown in the exploded view of FIG. 7B) configured to wrap around or hook to a portion of the pad 56 to secure the shim 366 to the pad 56 and maintain it in a desired position relative thereto. In some embodiments, the extensions 368 are curved to conform to the curvature of the pad 56 in a direction from the contact surface 56c to the surface opposite the contact surface to form a tight fit therewith upon installation of the shim 366. Although three extensions 368 are shown in the Figs. it is noted that one, two, or more than three extensions 368 could be used to secure the shim 366 to the pad 56.

In some embodiments the extensions 368 may be configured such that a space between the extensions 368 and the shim 366 into which the pad 56 will be received upon installation of the shim, is smaller than the space that will be occupied by the pad 56 upon installation. This causes the extensions 368 to be biased against the pad 56 when the shim is installed (see arrows in FIG. 7C, which is an end view of the posterior segment 164 and shim 366 of FIG. 7A) thereby securing the shim 366 in a desired position relative to the contact surface 56c of pad 56. Optionally the shim 366 may be further secured by installation of tacks, screws or other equivalent mechanical fixator 364 and/or adhesive 365, but these are not typically necessary and make it more difficult to remove the shim 366 in cases where it is desired to remove the shim 366 or replace the shim 366 with another shim 366 having different thickness characteristics.

Figure 7B:
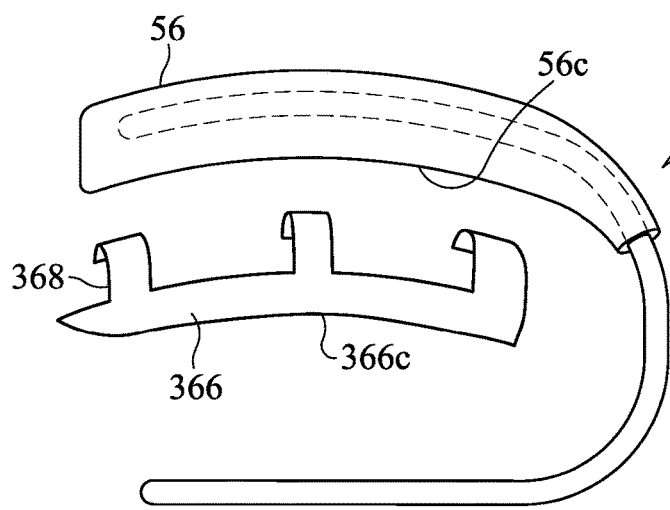
FIG. 7B is a partially exploded view of FIG. 7A.
Figure 7C:
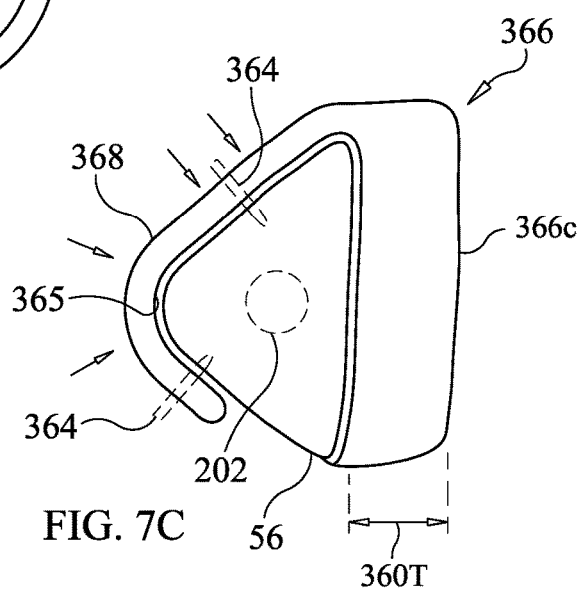
FIG. 7C is an end view of the posterior segment of FIG. 7A.
Figure 7D:
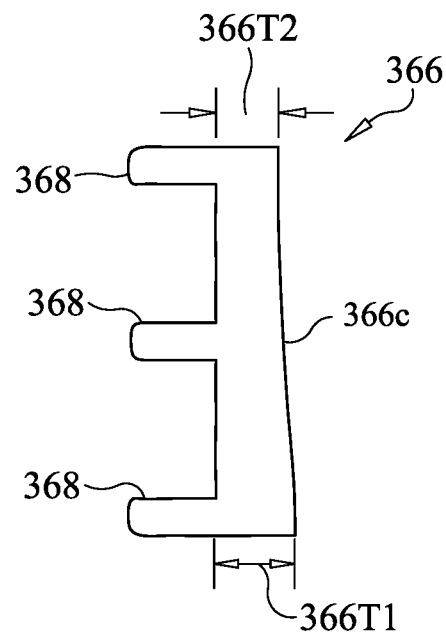
FIG. 7D is a top view of a shim according to an embodiment of the present invention.
Figure 7E:
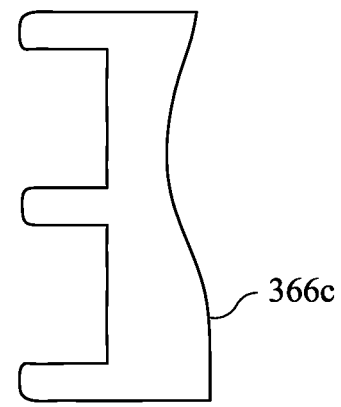
FIG. 7E is a top view of a shim according to another embodiment of the present invention.
Figure 7F:
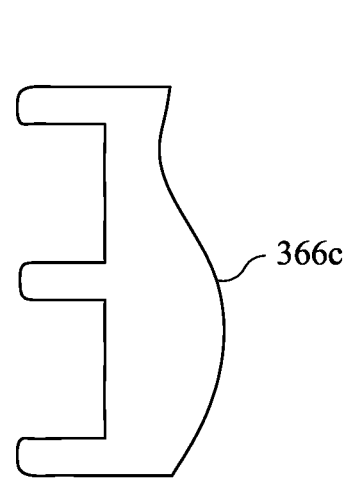
FIG. 7F is a top view of a shim according to another embodiment of the present invention.

In the embodiment shown in FIG. 7A-7C, shim 366 has a thickness 366T configured so that the contact surface 366c conforms to the shape of the contact surface 56c such that distance 72 varies from distance 70 by the same amount at all locations of the contact surface 366 relative to the corresponding locations on surface 56C. However, in other embodiments, the thickness 366T may vary over the shim 366 so as to vary the difference between distances 72 and 70 at different locations of the surface 366c so as to apply a different force profile to the tissue relative to the applied by contact surface 56*c*. FIG. 7D is a top view of a shim 366 in which the thickness 366T varies such that a distal end of the shim (end corresponding to the free end of posterior segment 164) has the greatest thickness 366T1 and the proximal end of the shim 366 has the least thickness 366T2. In this embodiment, the thickness change varies linearly from 366T1 to 366T2, but in other embodiments, the thickness can be varied according to any pattern desired in both the length and width directions of the contact surface 366*c*. For example, FIG. 7E shows an example in which the thickness is greatest at the distal end and the contact surface 366*c* is curved so that the minimal thickness is intermediate the proximal and distal ends and the thickness at the proximal end is greater than the intermediate minimum, but less than the maximum at the distal end. FIG. 7F shows an example in which the thickness is greatest (maximum thickness) at a distal end portion (inward of the distal end), the minimum thickness is at a proximal end portion (inward of the proximal end) and the proximal end thickness is about the same as the distal end thickness, less than the maximum thickness and greater than the minimum thickness. As noted, any other thickness variation pattern can be employed. Likewise, although the variations in the example of FIG. 7D-7F are shown only along the length dimension of the contact surface 366*c*, the same types of variations can be made in the thickness along the width dimension of the contact surface 366*c*.

Thickness 366T of the shim 366 may vary, and shims 366 may be provided in a kit having shims with different thickness characteristics. For example, one or more shims having thicknesses of 0.5 mm, 1 mm, 1.5 mm, 2 mm, 2.5 mm, 3 mm, 3.5 mm and 4 mm may be provided. However, these are only exemplary, and shim 366 may have a thickness 366T having any value between the stated values. Even thinner or thicker shims 366 could also be provided.

Figure 7G:
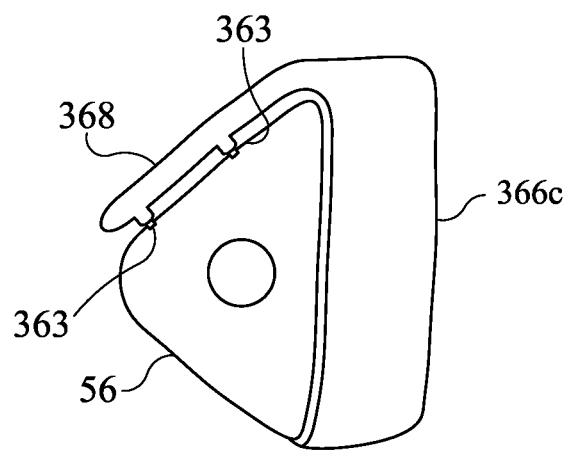
FIG. 7G is an end view of a posterior segment having a shim mounted thereto according to another embodiment of the present invention.

In using shim 366, device 10 is implanted against tissue/organ to be treated. Prior to or after anchoring device 10 to the tissue/organ (in the case of device 10A; in the case of device 10B the device will typically be anchored prior to installation of shim, although it need not be) manual manipulation of the device 10 can be carried out to form a space between the contact surface 56*c* and the tissue/organ that it was previously contacting. A shim 366 of desired configuration can then be installed over the pad 56 so that the contact surface 366*c* is positioned over the contact surface 56*c* to effectively extend the distance by which the resultant contact surface (366*c*) of the shimmed device 10 extends from the rod/rib 202. Extensions 368 are secured around the pad 56 as described above, by biasing forces provided by the extensions and/or mechanical securement means 364 and/or adhesive 365. FIG. 7G illustrates a free end view of an embodiment in which tacks 363 are integrated into extensions 368 so that once the shim 366 and extensions are positioned over the pad 56 as desired, application of pressure on the extensions 368 over the locations of the tacks 363 drives the tacks into the pad 56 for added securement of the shim 366. This embodiment also provides convenient reversibility, as the tacks 363 can be withdrawn from the pad 56 by simply pulling on the extension 368.

Procedurally the shim 366 can be used in the same manner as the manual adjustment mechanism described with regard to FIGS. 1A-1D, wherein visual observation can be made of the functioning of the tissue/organ to be treated both before and after installation of the shim 366 to determine whether the shim 366 has improved the functioning of the tissue/organ.

Figure 8A:
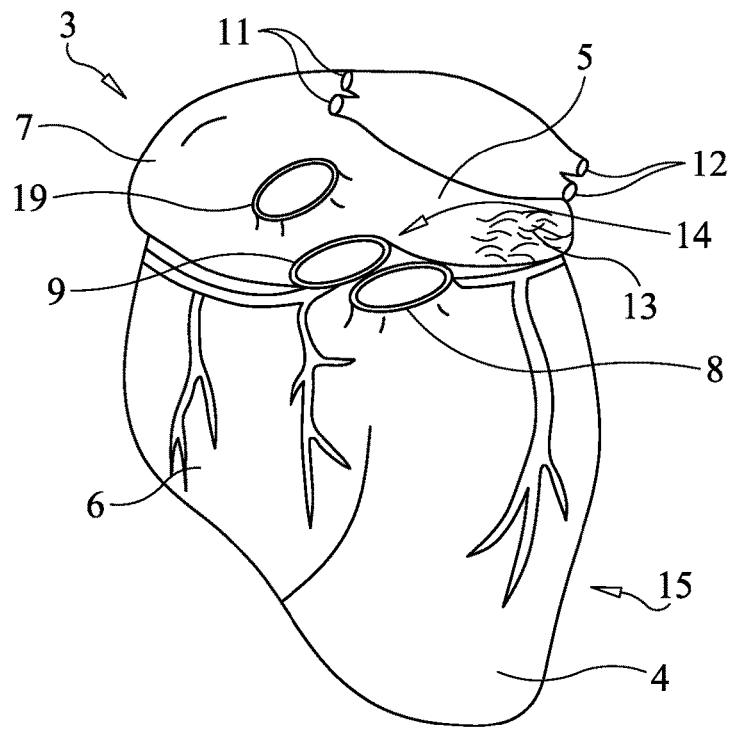
FIGS. 8A-8B are illustrations of a human heart, with the illustration in FIG. 8B viewed with the pericardium removed.
Figure 8B:
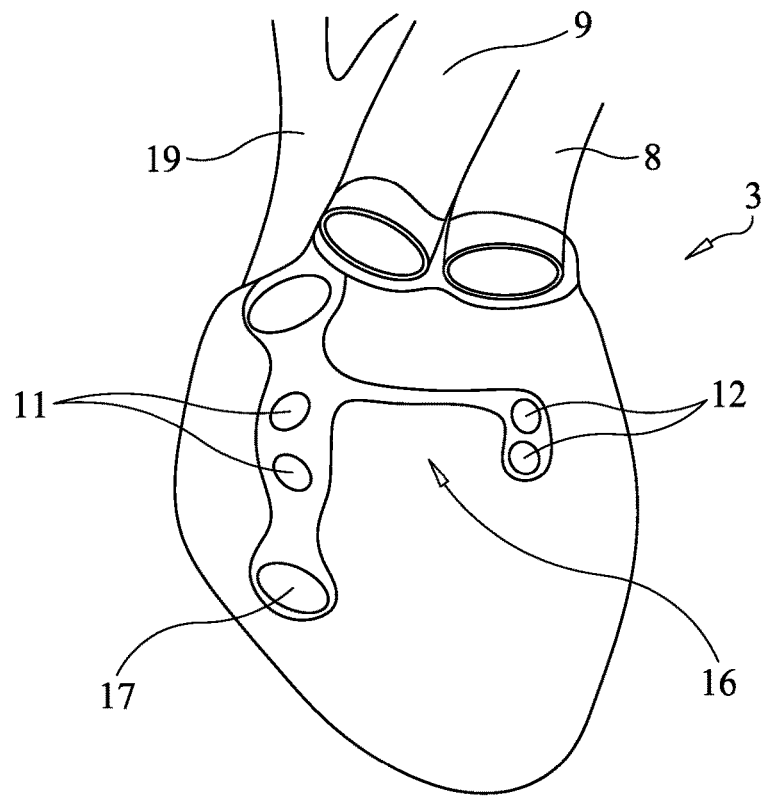

FIGS. 8A-8B are illustrations of a human heart 3, with the illustration in FIG. 8B viewed with the pericardium 15 removed. The chambers of the heart 3 include the left ventricle 4, the left atrium 5, the right ventricle 6, and the right atrium 7, as shown. Also shown are the pulmonary trunk 8, the aorta 9, the superior vena cava 19, the right pulmonary veins 11, the left pulmonary veins 12, and the left atrial appendage 13. The transverse sinus 14 is also referenced in FIG. 8A. The transverse sinus 14 is a pericardial cavity between the pericardium 15 and the epicardial surface of the heart 3 located posterior to the aorta 9 and the pulmonary trunk 8 and anterior to the left atrium 5 and the superior vena cava 19. The pericardial sac or pericardium 15, which is a tissue membrane covering the epicardial surface of the heart 3, is also shown removed from the heart H in FIG. 8B to further illustrate noteworthy anatomy of the heart 3. The oblique sinus 16 is a blind (e.g., cul-de-sac) recess on the posterior of the heart 3 formed between the pericardium 15 and the epicardial surface of the heart 3. The oblique sinus 16 lies generally between the right pulmonary veins and 11 and the left pulmonary veins 12, with the thoracic part of the inferior vena cava 17 located on the side of the pulmonary veins 11. Only two layers of serous pericardium separate the transverse sinus 14 and the oblique sinus 16.

The devices described herein may be positioned on the epicardial surface of the heart 3 during a medical procedure. For example, in some embodiments the device 10 (referring to embodiments 10A, 10B and all other devices reference by 10 and a letter) may be installed on the heart 3 during a heating heart surgery, without the need of a heart/lung bypass machine. For instance, the device 10 may be implanted on the heart 3 through an open chest procedure (sternotomy) or a lateral thoracotomy. In some embodiments, the device 10 may be positioned on the heart 3 through a less-invasive endoscopic approach. For example, during a sternotomy, the thoracic cavity may be accessed for direct visual placement of the device 10 on the beating heart 3. For any of these procedures, the pericardium 15 may be incised to access the pericardial cavity between the pericardium 15 and the epicardial surface of the heart 3. Upon accessing the pericardial cavity, the device 10 may be properly positioned on the epicardial surface of the heart 3.

Figure 9A:
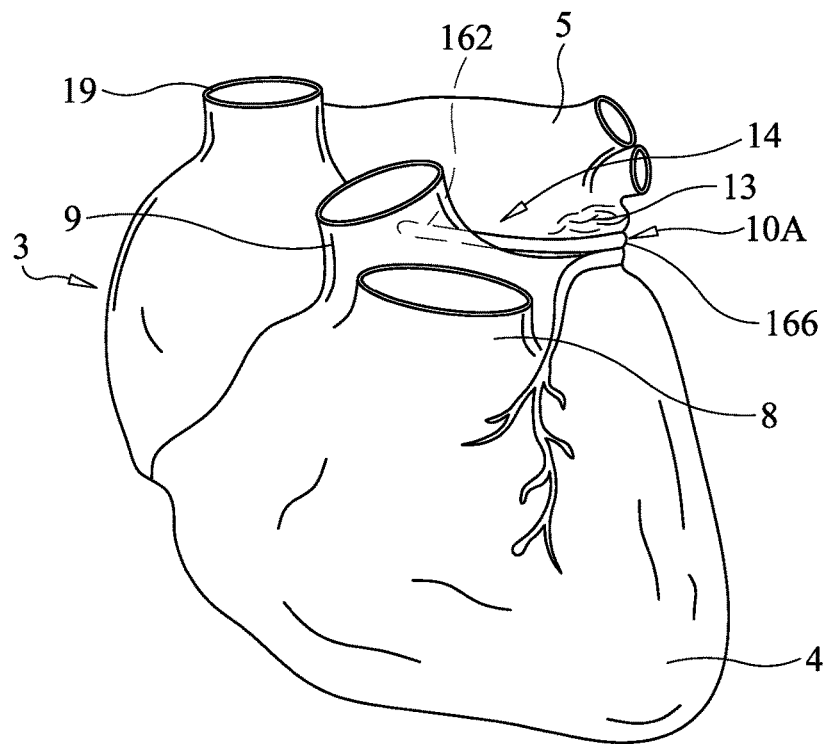
FIGS. 9A-9B illustrate locations of placement of a device epicardially on a heart according to an embodiment of the present invention.

For example, in the case of device 10A, FIG. 9A is an anterior view of the heart 3, with the device 10A placed on the epicardial surface of the heart 3. As shown in FIG. 9A, the anterior segment 162 of the device 10A is positioned in the transverse sinus 14 posterior to the aorta 9 and the pulmonary trunk 8 and anterior to the left atrium 5 and the superior vena cava 19. The lateral segment 166 may extend around the left lateral side of the heart 3 at a location inferior to the left atrial appendage 13. In other embodiments, the lateral segment 166 may extend around the left lateral side of the heart 3 at a location superior to the left atrial appendage 13 or over the left atrium 5.

Figure 9B:
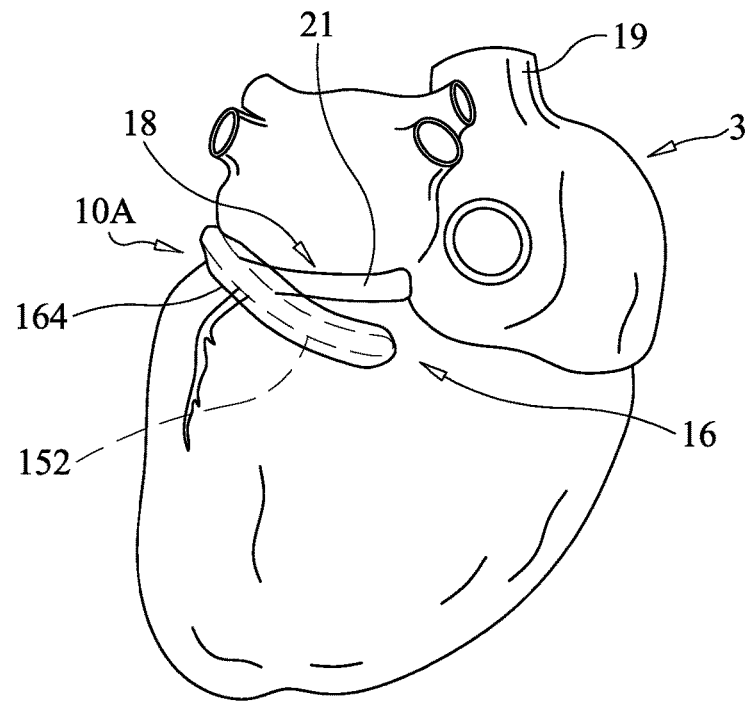

FIG. 9B is a posterior view of the heart 3 with the device 10A placed on the epicardial surface of the heart 3. As shown in FIG. 9B, the posterior segment 164 of device 10A is positioned on the posterior of the heart 3 inferior of the atrioventricular groove 18. The posterior segment 164 may be positioned such that it is just below the circumflex artery 21. In other embodiments, the posterior segment 164 may be positioned such that it is just above the circumflex artery 21.

Thus, the anterior segment 162 may be located in the transverse sinus 14. The posterior segment 164 may be positioned on the posterior side of the heart 3, such as on or inferior to the atrioventricular groove 18 or in the oblique sinus 16. In some embodiments, the posterior segment 164 may be positioned inferior to the atrioventricular groove 18 on the posterior side of the heart 3. The lateral segment 166 may extend around the left lateral side of the heart 3 such that the anterior segment 162 is properly positioned in the transverse sinus 14 while the posterior segment 164 is properly positioned on the posterior side of the heart 3, such as on or inferior to the atrioventricular groove 18 or in the oblique sinus 16. In some embodiments, the lateral segment 166 may extend around the heart 3, at a location inferior to the left atrial appendage 13. However, in other embodiments the lateral segment 166 may extend around the heart 3 at a location superior to the left atrial appendage 13 or over the left atrium 5 to join the anterior segment 162 and the posterior segment 164. The anterior and posterior ends are spaced apart from one another by a predetermined distance and remain separated by a gap or opening after completion of implantation of the device 10A.

The devices 10 of the present invention, when properly positioned, may reside on the epicardial surface of the heart 3, interior of the pericardium 15. Thus, positioning of the device 10 may not require penetration of the heart into one or more of the chambers of the heart and/or may not require the device 10 to come into contact with blood being located inside the chambers of the heart 3. By placing the device 10 on the epicardial surface, exterior of the interior of the heart 3, complications associated with surgical procedures in which access is required to one or more of the chambers of the heart 3 are avoided. Furthermore, the time required to complete the surgical procedure may be greatly reduced from the time required for an open heart surgery or a surgical procedure requiring accessing the heart 3 through the vasculature.

The device 10 of the present invention is configured for manual adjustment thereof in manners described herein to enable it to adjust the distance between portions of the device and ultimately, to adjust the amount of force applied to the tissue/organ/heart so as to reform/reshape target tissues by an extent that successfully improves the functioning of the target tissue/organ. In some embodiments, the configuration of device 10 can be manually adjusted in order to adjust forces applied to a heart 3 so as to alter the geometry of an annulus of a valve of the heart 3 and thereby adjust the coaptation of the leaflets of the valve. Echocardiographic images may be taken prior to selection of a device to ascertain a configuration of a device to be used, after installation of the device (including before and/or after anchoring of the device) to ascertain whether the implantation of the device has achieved a satisfactory result, and, in cases where a satisfactory result has not yet been achieved, after manual adjustment of the device to confirm whether the adjustment has achieved a satisfactory result. In cases where heart valve regurgitation is being treated, a satisfactory result may be a significant reduction or elimination of mitral valve regurgitation, wherein the significant reduction may result in 50%, 60%, 70%, 80%, 90% or 100%, or any value therebetween of the volume of blood which was being regurgitated prior to the installation of the device 10.

For example, as described above, the distance 70 between the rod/rib 202 and the contact surface of device 10A can be increased or decreased by repositioning the rod/rib relative to the pad 56 as described with regard to FIGS. 1A-3B, or distance 70 can be increased by attaching a shim 366 in a manner as described above with regard to FIGS. 7A-7G.

Figure 10:
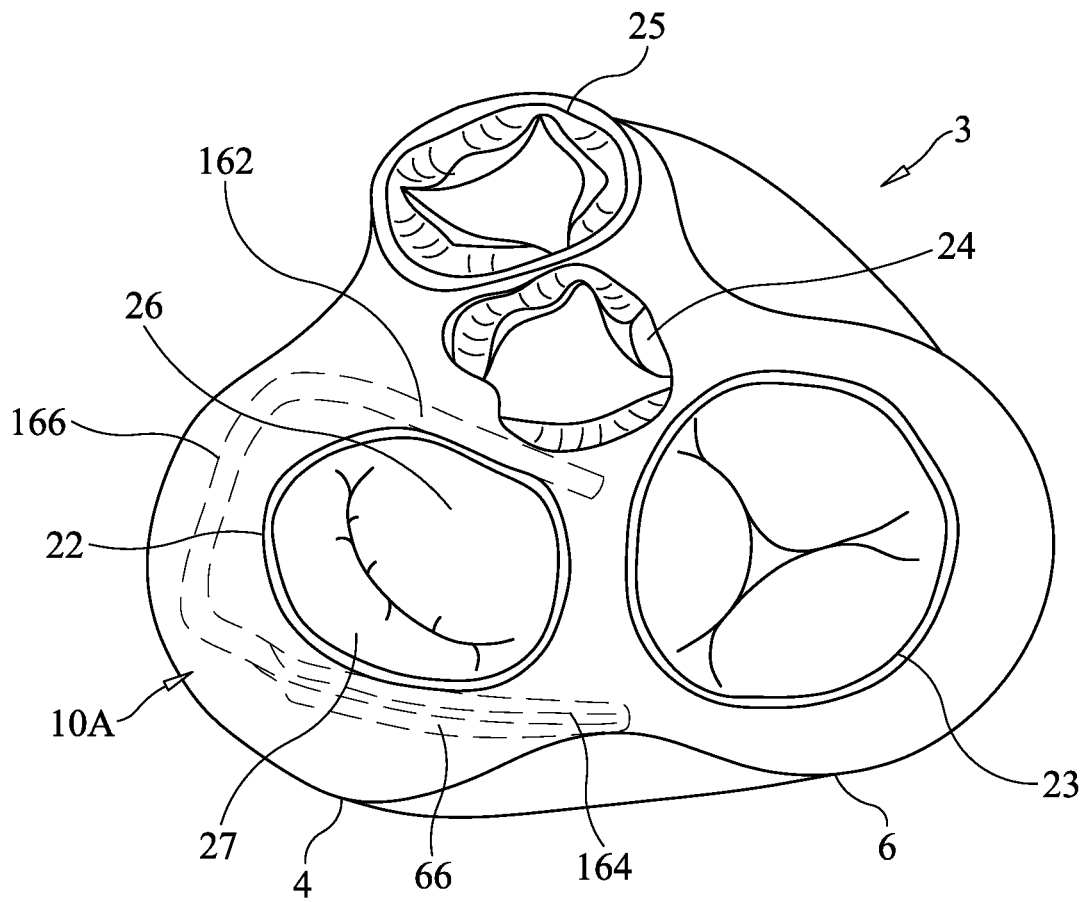
FIG. 10 is a top view of the ventricular portion of a heart, with the atria removed, and illustrating a device in phantom, according to an embodiment of the present invention.

FIG. 10 is a top view of the ventricular portion of the heart 3 with the atria removed. With the atria removed, the mitral valve 22 between the left atrium 5 (not shown in FIG. 10) and the left ventricle 4 is clearly shown. Also shown is the tricuspid valve 23 between the right atrium (not shown in FIG. 10) and the right ventricle 6, as well as the aortic valve 24 leading to the aorta 9 and the pulmonary valve 25 leading to the pulmonary trunk 8. As shown in FIG. 10, the mitral valve 22 includes two leaflets, an anterior leaflet 26 and a posterior leaflet 27. The mitral valve 22 is shown closed as it would be during systole. The device 10A is shown in phantom (dashed lines) in FIG. 10 as the device 10A may not lie in the plane of the mitral valve 22 shown.

When device 10A is properly placed around the heart 3 as illustrated in FIG. 10, the shape of the device 10A may reduce the anterior-posterior measurement of the mitral valve 22. In other words, the device 10A may urge the posterior leaflet 27 of the mitral valve 22 and anterior leaflet 26 toward one another, providing better contact (coaptation) of the anterior 26 and posterior 27 valve leaflets of the mitral valve 22, which may reduce or eliminate mitral regurgitation. Device 10A is manually adjustable in ways already described above to alter the distance between the anterior segment 162 and posterior segment 164 through operation of either repositioning the rod/rib 202 relative to the pad 56 or installation of a shim 366 to move the contact surface 56c (or 366 in a case where a shim 366 is installed) closer to the anterior segment 162, to further urge the leaflets 26 and 27 together. Alternatively, manual adjustment of the device 10A could be performed by removing a shim 366 or repositioning the rod/rib 202 relative to the contact surface 56c in a manner described above to increase the distance between anterior segment 162 and posterior segment 164 if needed, such as in a case where bringing the leaflets too close to one another could possible worsen mitral regurgitation. Thus, the placement of device 10A as shown in FIG. 10 can be installed in a manner to initially reduce or eliminate mitral valve regurgitation.

A method of treating mitral valve regurgitation as one preferred example of various methods of treatment that may be used to treat mitral valve regurgitation is now provided. In addition to variations of this method described, as well as variations in the particular device 10 used, it is further noted that the present devices are not limited to the treatment of mitral valve regurgitation, as they could be used to treat tricuspid valve regurgitation or regurgitation in another heart valve other than the mitral and tricuspid valves, and further could alternatively be used to treat any of the tissues/organs identified herein.

In one embodiment, a method of installation of device 10A as shown in FIG. 10 may include providing the device 10A and positioning the anterior and posterior segments 162, 164 epicardially on the heart 3 at locations apposite to an annulus of the mitral valve 22, such that the anterior 162 and posterior 164 segments apply force sufficient to reshape the annulus of the mitral valve 22. The device 10A may then be anchored in this proper position using tissue anchors 54 as described previously. Visual observation, such as by echocardiography, or other visualization technique can be used to observe blood flowing through the mitral valve to determine whether the mitral valve regurgitation (retrograde flow of blood from the left ventricle through the mitral valve 22 to the left atrium) has been successfully reduced or eliminated. If it is determined that the mitral valve regurgitation has been successfully reduced or eliminated, the implantation is complete and the patient can be closed up according to known and accepted procedures to include the implantation procedure.

If it is observed that the mitral valve regurgitation has not been successfully reduced or eliminated, the device 10A can then be manually adjusted to alter the force (and amount of deformation of the heart wall which directly affects the amount of reformation of the mitral valve annulus) applied by the device 10A. This can be achieved using any of the techniques, mechanisms and features described herein, such as by manually adjusting the position of rod/rib 202 relative to contact surface 56c in the posterior segment 164 as described above, or by installing a shim 366 as described above.

Once the manual adjustment has been performed and the adjusted contact surface 56c or contact surface 366c is in contact with the posterior wall of the heart 3, visual observation is again performed to visually confirm whether the mitral valve regurgitation has been successfully reduced or eliminated. If it is determined that the mitral valve regurgitation has been successfully reduced or eliminated, the implantation is complete and the patient can be closed up according to known and accepted procedures to include the implantation procedure.

If it is determined that the mitral valve regurgitation has not been successfully reduced then further procedures are required at this stage, which may involve further adjusting the rod/rib distance relative to the contact surface; removing the shim 366 and replacing it with another shim having a different thickness and or conformation.

If manual adjustments of the device 10A cannot achieve successful reduction or elimination of mitral valve regurgitation, then the device 10A may need to be removed and replaced with another device, such as a device having different dimensions, including, but not limited to the distance between the anterior 162 and posterior 164 segments.

Prior to the initial installation of device 10A above, the procedure may further involve applying force to a posterior surface of the heart while visually observing blood flow through the mitral valve 22. The applied force may be varied, in magnitude and/or its location of application in an effort to find the magnitude and location that will successfully reduce or eliminate mitral valve regurgitation. When it is observed that the mitral valve regurgitation has been successfully reduced or eliminated, the video image at this time can be used to measure the distance between the external wall surfaces of the heart 3 where the anterior 162 and posterior 164 segments of device 10A are intended to be placed. From this measurement, an appropriately sized device 10A that has a distance between the anterior 162 and posterior 164 segments that is configured to establish a distance between the external heart walls as measured can be selected for the installation.

Figure 11:
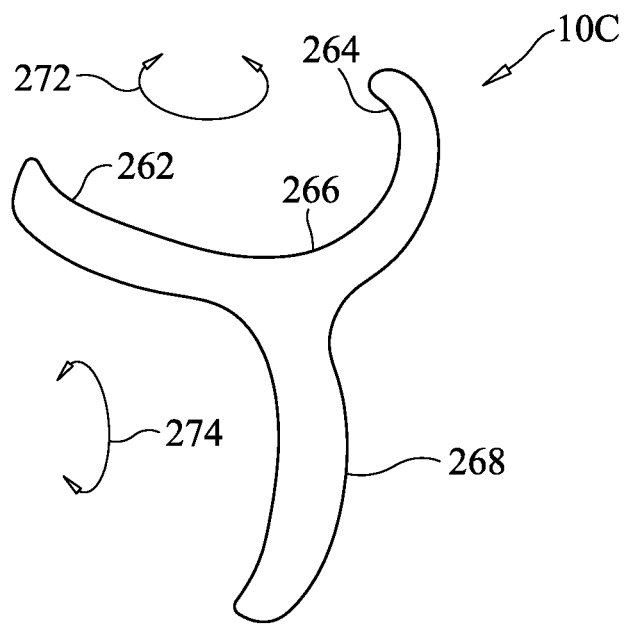
FIG. 11 illustrates an implantable device according to another embodiment of the present invention.

FIG. 11 shows a device 10C according to another embodiment of the present invention. In this embodiment, device 10C includes anterior or first segment 262, posterior or second segment 264 and lateral or third segment 266 interconnecting the segments 262 and 264. Additionally, an inferior or fourth segment 268 extends from the lateral segment 266 in a direction transverse to a direction along which the first, second and third segments 262, 264, 266 extend. As shown, segment 268 extends in a direction substantially normal to the direction in which at least one of anterior segment 262, posterior segment 264 and lateral segment 266 extend, but the angulation may vary between about sixty degrees and one hundred twenty degrees.

The manual adjustment mechanism described with regard to FIGS. 1A-3B (including rod/rib 202, channel 66 and restrictions/stops 68) may be provided in one or both of posterior 364 and inferior 268 segments. The structure and materials used for making device 10C may be the same as for those used for devices 10A and 10B. Alternatively or additionally, a shim 366 may be installed over one or both of posterior 264 and inferior 268 segments in any manner described above.

Accordingly, device 10C may be configured to manually adjust posterior segment 264 and/or inferior segment 268. Manual adjustment of posterior segment can be carried out to change the configuration and/or force applied by the device 10C in a first plane (indicated by arrows 272), and manual adjustment of the inferior segment 268 can be carried out to change the configuration and/or force applied by the device 10C in a second plane (indicated by arrows 274). The first and second planes may be normal to one another, but need not be and are not coplanar.

Figure 12:
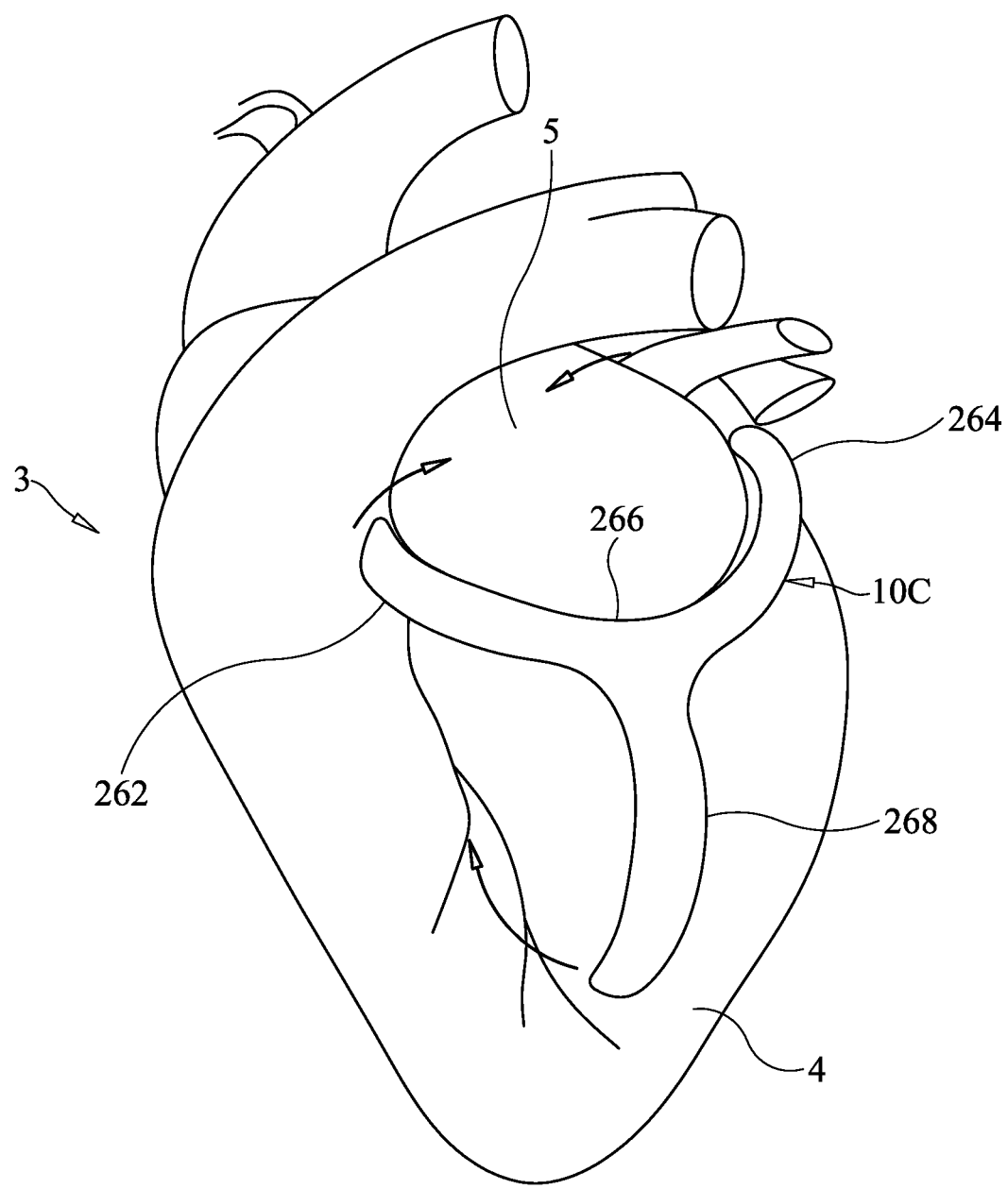
FIG. 12 illustrates an example of use of the device of FIG. 11 on a heart for treatment of mitral regurgitation, according to an embodiment of the present invention.

FIG. 12 illustrates an example of use of device 10C on a heart 3 for treatment of mitral regurgitation. The anterior, lateral and posterior segments 262, 266 and 264 are positioned epicardially on the heart 3 in an orientation permitting these segments to apply forces to the heart 3 that transfer to the mitral valve annulus and mitral valve, so as to reshape the same to reduce or eliminate mitral regurgitation, in manners already described above. In some embodiments, the anterior segment 262 may be substantially straight, and thus capable of residing in the transverse sinus of the heart 3. In some embodiments, the posterior segment 264 may be arcuate, corresponding to the convex curvature of the posterior ventricular wall of the heart 3. The lateral segment 266 interconnects the anterior 262 and posterior 264 segments with a sufficient length to establish the appropriate distance between the segments 262 and 264 for effectively applying force to the mitral valve annulus to cause a reduction or elimination of mitral valve regurgitation. Device 10C may be configured so that the lateral segment 266 can be routed around the left lateral side of the heart, placing the anterior segment 262 in the transverse sinus and the posterior segment 264 on the posterior of the heart 3, such as on or inferior to the atrioventricular groove or in the oblique sinus of the heart 3. In some embodiments the lateral segment 266 may be routed around, over and/or under the left atrial appendage of the heart 3. In other embodiments, the lateral segment 266 may be routed over the left atrium 5 of the heart 3.

The inferior segment 268 extends inferiorly from the lateral segment 266 and is positioned along a portion of the length of the ventricle 4 as illustrated in FIG. 12, so that force applied by the inferior segment epicardially to the wall of the left ventricle is in an amount and location (e.g., apposite to or inferior to one or more locations of insertion of chordae tendineae 28/papillary muscle 29 into the inner wall of the ventricle 4) to reduce tension on the chordae tendineae.

Figure 13:
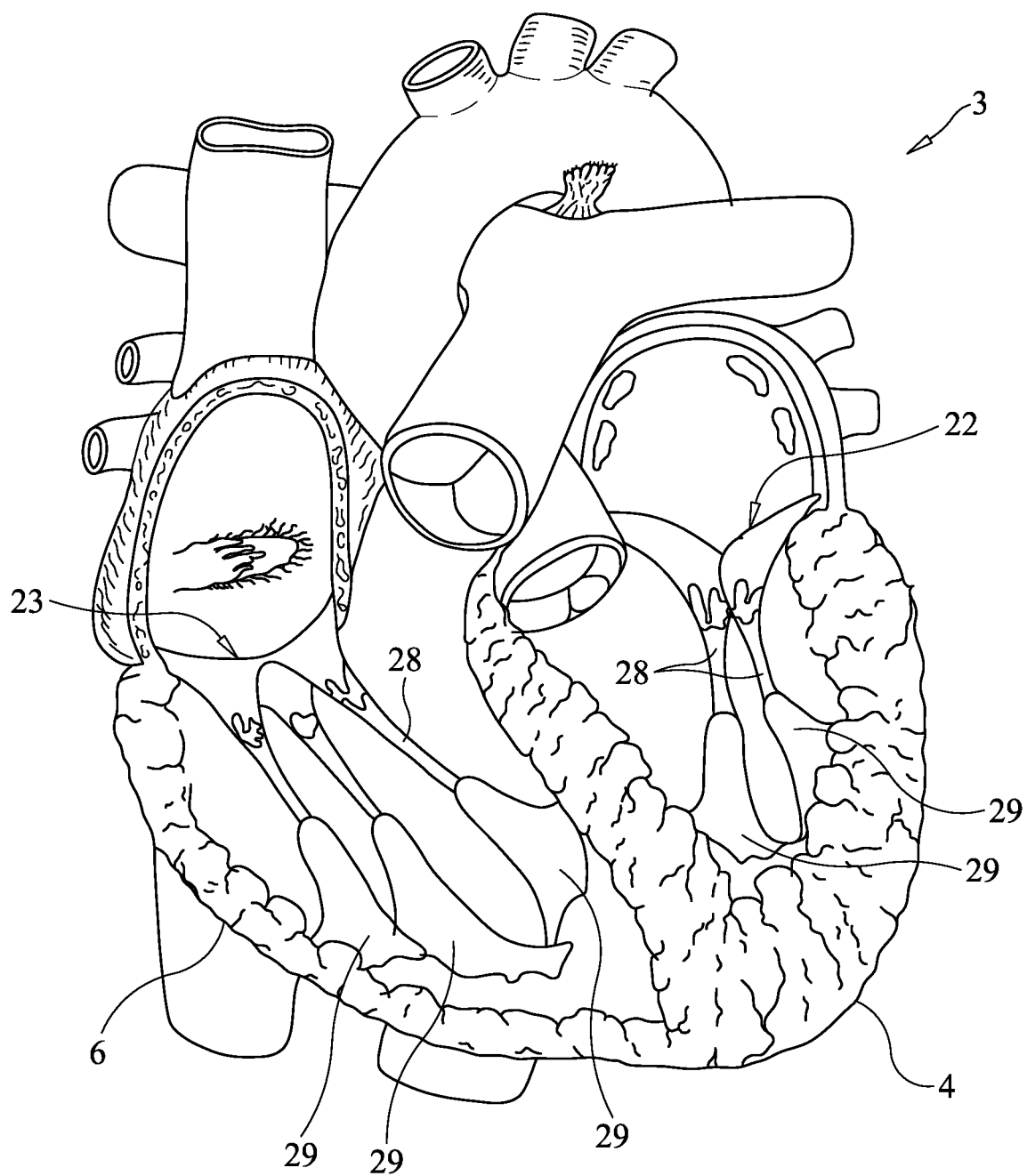
FIG. 13 is a cutaway view of a human heart illustrating chordae tendineae and papillary muscles in the left and right ventricles.
Figure 14:
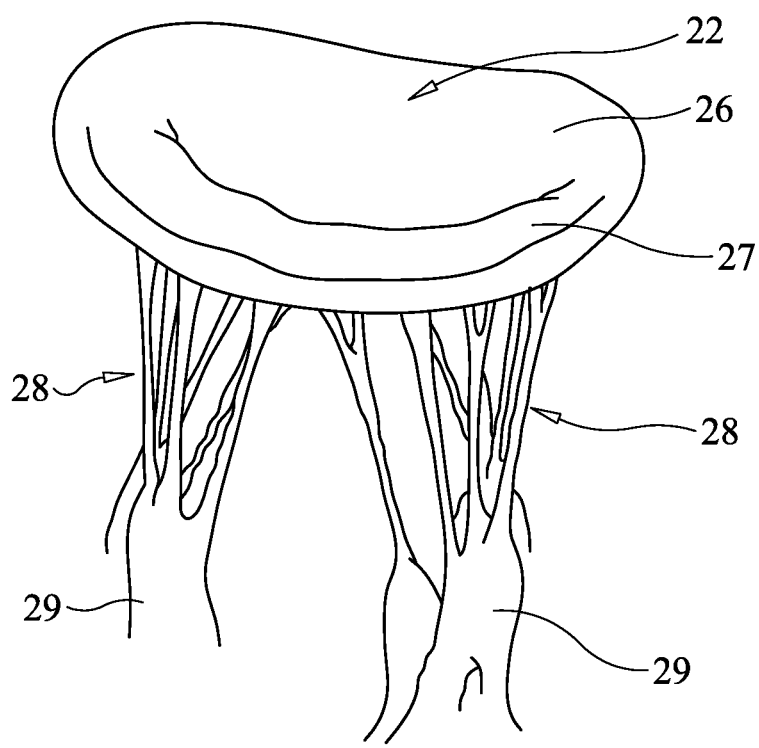
FIG. 14 is an isolated view showing attachment of the papillary muscles to the anterior leaflet and posterior leaflet of the mitral valve via chordae tendineae.

FIG. 13 is a cutaway view of a human heart illustrating chordae tendineae 28 and papillary muscles in the left 4 and right 6 ventricles. The papillary muscles 29 in the left ventricle 4 attach to the cusps of the mitral valve 22 and the papillary muscles 29 in the right ventricle 6 attach to the cusps of the tricuspid valve 23 via the chordae tendineae 28. FIG. 14 is an isolated view showing attachment of the papillary muscles 29 to the anterior leaflet 26 and posterior leaflet 27 of the mitral valve 22 via chordae tendineae 28. The papillary muscles 29 contract to prevent inversion or prolapse of the mitral valve leaflets 26, 27 (likewise, to prevent inversion or prolapse of the tricuspid valve leaflets by 29, 28 in the right ventricle) during systole (or ventricular contraction). The papillary muscles 29 of both the right 6 and left 4 ventricles begin to contract shortly before ventricular systole and maintain tension throughout. In the case of a normal heart 3 and heart valves, this prevents regurgitation, backward flow of ventricular blood into the atrial cavities, by bracing the atrioventricular valves against prolapse (prolapse described by being forced back into the atria by the high pressure in the ventricles).

However, in some cases of mitral and/or tricuspid regurgitation, the papillary muscles 29 and/or chordae tendineae may apply too much contraction against the valve leaflets, either due to shortening of the chordae tendineae 28/papillary muscles 29 compared to normal or other reason. In these instances, reduction and or prevention of regurgitation may be helped or accomplished reducing the amount of contraction or force applied through the chordae tendineae 28. For example, manual adjustment of inferior segment 268 to apply greater force to and deformation of the epicardial wall of the left ventricle 4 may cause a relative reduction in tension on the chordae tendineae 28, which, as a result will allow better closure of the mitral valve leaflets 26,27 during systole, thereby reducing or eliminating mitral valve regurgitation. In combination with the reshaping accomplished by forces applied to the mitral valve annulus by the anterior and posterior segments 262, 264, the forces applied to the ventricle 4 to reduce tension on the chordae tendineae 28 may cooperate to reduce or eliminate mitral regurgitation. It is further noted that the device 10C could be adapted for similar functioning to reduce or eliminate tricuspid regurgitation from the right ventricle 6 through the tricuspid valve 23.

In the use case shown in FIG. 12, manual adjustment of the posterior 264 and inferior 268 segments work in two areas: (1) around the annulus of the mitral valve 22; and (2) against the anterior chordae tendineae 28. By applying forces to these two areas as described, compression of the anatomy is achieved. Around the mitral valve 22, the compression will serve to help close the mitral valve 22. In the area of the chordae tendineae 28, compression will serve to reduce tension on the chordae tendineae 28, which will in turn reduce the tendency toward opening of the mitral valve 22. Both mechanisms can serve to reduce mitral valve regurgitation.

Figure 15:
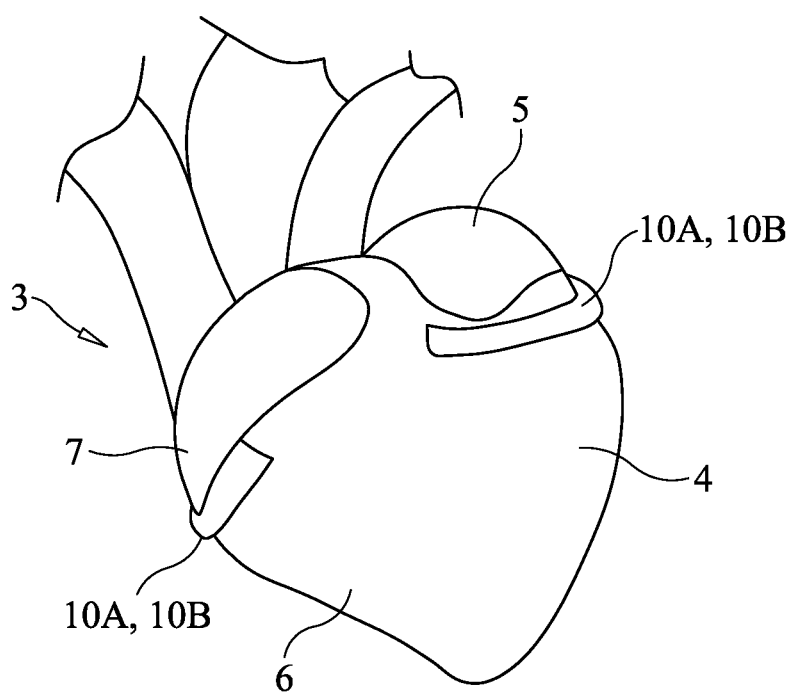
FIG. 15 illustrates various applications of devices of the present invention for use epicardially on the heart, according to embodiments of the present invention.

FIG. 15 illustrates various applications of the devices of the present invention for use epicardially on the heart 3. As already described, device 10A or 10B can be installed epicardially between the left ventricle 4 and left atrium 5 to treat mitral valve regurgitation. Additionally, or alternatively, device 10A or 10B can be configured for installation between the right ventricle 6 and right atrium 3 to treat tricuspid valve regurgitation.

Figure 16:
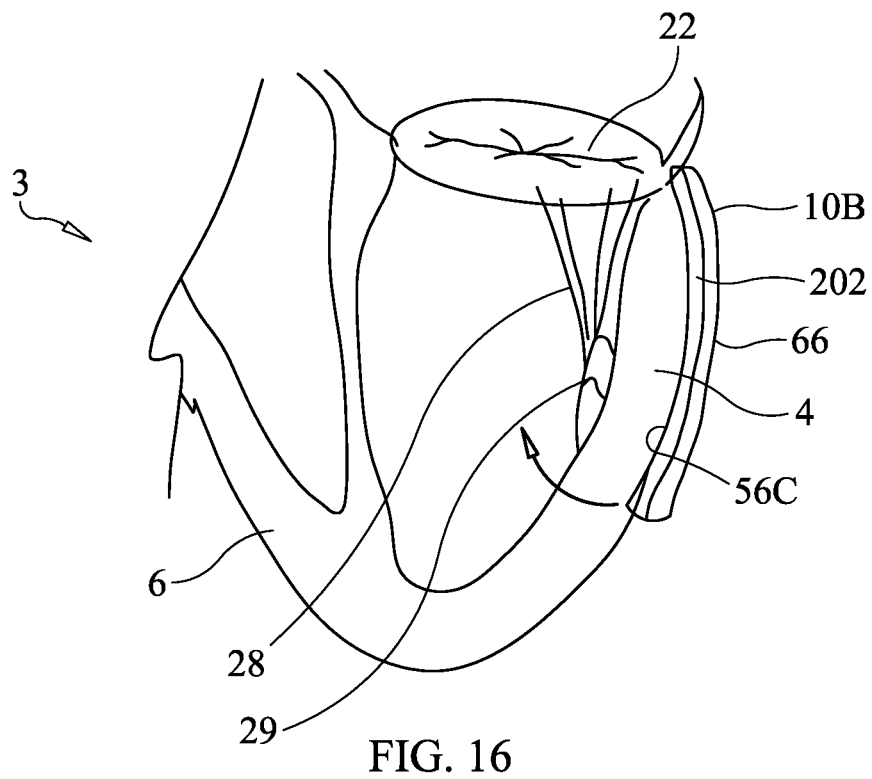
FIG. 16 is a partial, sectional view of a heart on which a device is epicardially installed for treatment of mitral valve regurgitation, according to an embodiment of the present invention.

FIG. 16 is a partial, sectional view of a heart 3 on which device 10B is epicardially installed for treatment of mitral valve regurgitation, according to an embodiment of the present invention. The device 10B when properly positioned, extends inferiorly from a location at or about the level of the mitral valve 22 and is positioned along a portion of the length of the ventricle 4, so that a distal end portion thereof is positioned over or inferior of an epicardial location of the ventricle 4 that is apposite to one or more locations of insertion of chordae tendineae 28/papillary muscle 29 into the inner wall of the ventricle 4. After anchoring the device 10A using tissue anchors as described above, device 10B can be manually adjusted to change the amount of force applied thereby, such as by changing the position of rod/rib 202 relative to relative to contact surface 56c in the embodiment shown, or, alternatively or additionally, by installation of a shim 366 in a manner described previously. Increase of force against the epicardial wall of the ventricle 4 by device 10B may cause additional inward deformation of the wall and a consequent reduction in tension on the chordae tendineae 28, which, as a result may allow better closure of the mitral valve leaflets 26,27 during systole, thereby reducing or eliminating mitral regurgitation.

Figure 17A:
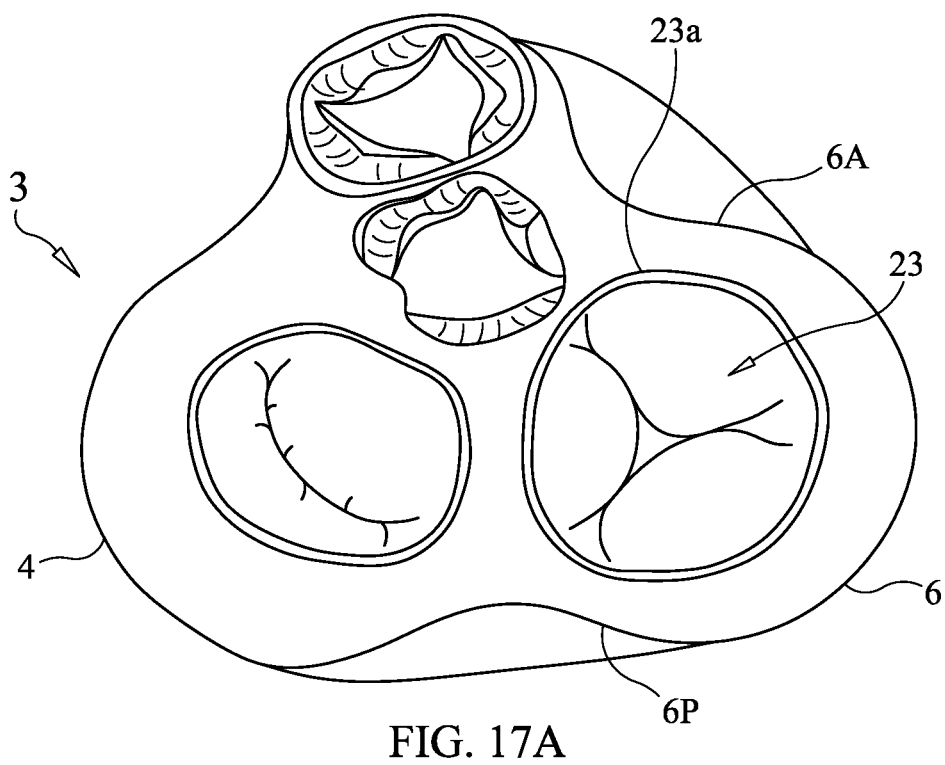
FIG. 17A-17B schematically illustrate events that may be carried out during an implantation of a device according to an embodiment of the present invention.
Figure 17B:
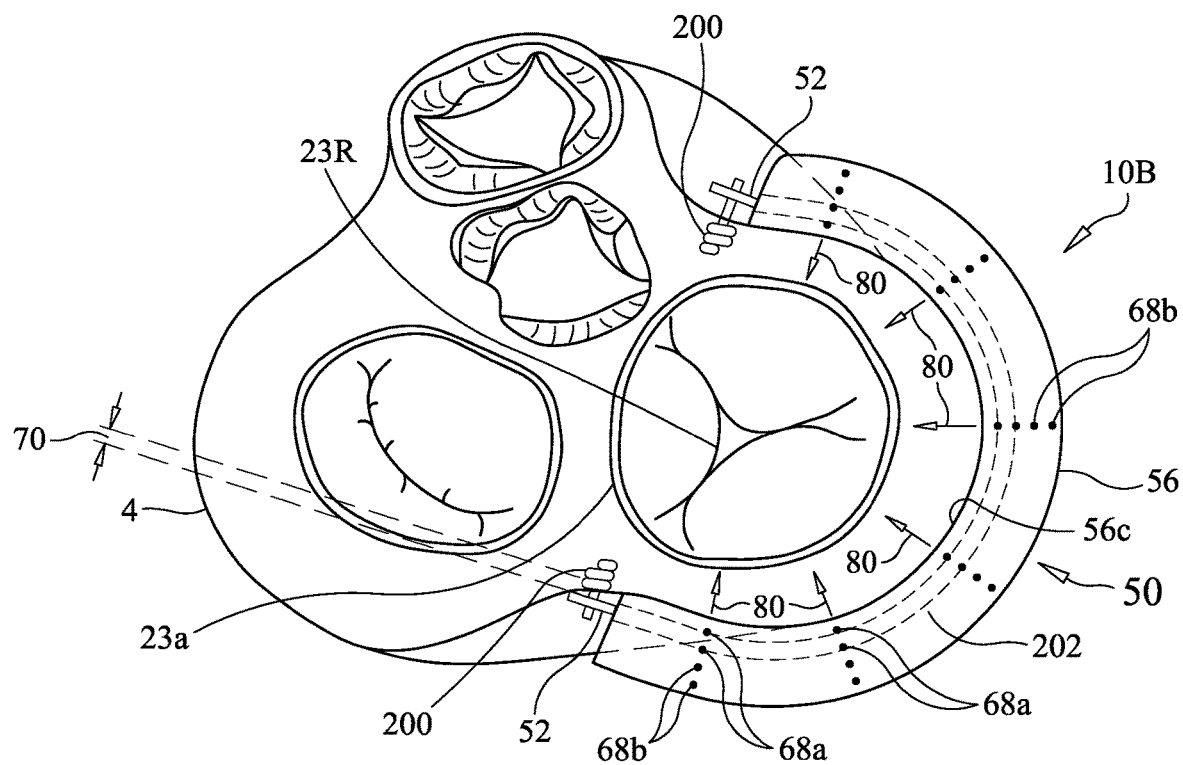

FIG. 17A-17B schematically illustrate events that may be carried out during an implantation of a device 10B according to an embodiment of the present invention. Optionally, an initial measurement to determine a distance between an epicardial surface 6P of the posterior wall of the right ventricle at a level in or about a plane of the tricuspid valve 23 and an epicardial surface 6A of the anterior wall of the right ventricle 6 at a level in or about the plane of the tricuspid valve 23 can be made in a manner like that described above when measuring the distance 160 for use on the left side of the heart, using any of the instruments and techniques described in International Application Serial No. PCT/US2019/015300, except the forces applied are forces to the right ventricle 6 to measure the distance needed for treatment of the tricuspid valve 23. Alternatively, this measurement step can be skipped. In either case, the device 10B that is implanted for the treatment can be adjusted during or after implantation to change the amount of force/displacement of the wall of the ventricle 6 and thus to the annulus of the tricuspid valve. During this force adjustment, visualization, such as by transesophageal electrocardiography (TEE), for example, can be used to monitor the tricuspid valve 23 and visualize the amount of regurgitation therethrough, to determine when the optimum amount of force/displacement has been reached.

Once a distance measurement has been made, if that option is chosen, a device 10B having appropriate distance characteristics is attached epicardially, in or about the plane of the tricuspid valve 23, as illustrated in FIG. 17B. FIG. 17B illustrates device 10B having been installed epicardially on the heart 3 of a patient for treatment of tricuspid valve regurgitation as one of the preferred embodiments of location of implantation. In this preferred embodiment, device 10B can be installed epicardially on the heart 3 over a target location to effect reshaping of the tricuspid valve annulus 23a. The device 10B (as well as the device 10D of FIG. 18) can be installed with the fixators 200 pre-mounted to the device so that the device is attached to the target tissue simultaneously with the anchoring of the fixators 200. Alternatively the fixators 200 can be anchored prior to introducing the device and the device can subsequently be attached to the implanted fixators 200 to anchor the device to the target tissue. Preferably, the contact pad 56 of the device is as long as can be fitted to the heart 3 at this location, so that the contact surface 56C of the pad contacts the heart wall around as much of the tricuspid valve annulus 23a as possible. FIG. 17B shows that the pad 56 of the device 10B surrounds greater than 50% of the annulus 23a and can apply forces to three sides of the heart wall (anterior, posterior and lateral). Preferably the pad 56 extends as far as is physically possible before it is prevented by heart structures from extending any further. Thus, the pad may surround a percentage of the annulus in a range from 30% to 70%, preferably 40% to 70%, more preferably 50% to 70%, even more preferably 60% to 70%. The clinical benefit is not constrained by these percentages as this epicardial approach with allow for tuning of the clinical benefit based on the patient specific anatomy. The device 10B may be anchored to the wall of the heart at the level of the tricuspid valve 23 via fixators 200 in a manner as described with regard to previous embodiments described.

Rod/rib 202 extends through the main body 50 of device 10B and forms extension rods 52 that extend from both ends of main body 50. Rod/rib 202 is preferably substantially curved as shown, with a curvature configured to conform to the curvature of the epicardial walls of the right atrium 6 at the level of the tricuspid valve 23 on an the epicardial surfaces exposed that the patient's anatomy presents. The main body is formed by pad 56 which surrounds or encases the portion of the rod/rib 202 extending therethrough.

Extension rods 52 can be configured to engage with fixators 200. Optionally, one or more fixators 200 could be applied through the pad 56, intermediate the ends of the device 10B to further secure the device 10B to the tissue. As noted above, rod/rib 202 (which includes extension rods 52) is rigid.

In FIG. 17B, the rod/rib 202 is shown captured by the stops 68a, such that the normal distance measurement between rod/rib 202 and the location of the contact surface 56C is 70 and a force 80 applied to the external wall of the heart 3 results in a deformation of the heart wall and annulus 23a of the mitral valve 23. Note that forces 80 are applied all along the heart wall where the contact surface 56C extends. For exemplary purposes, FIG. 17B illustrates that the valve leaflets of the tricuspid valve 23 have not been completely closed by this reshaping of the tricuspid valve annulus 23a, where a small separation 23R remains between the leaflets to allow some tricuspid valve regurgitation.

Figure 17C:
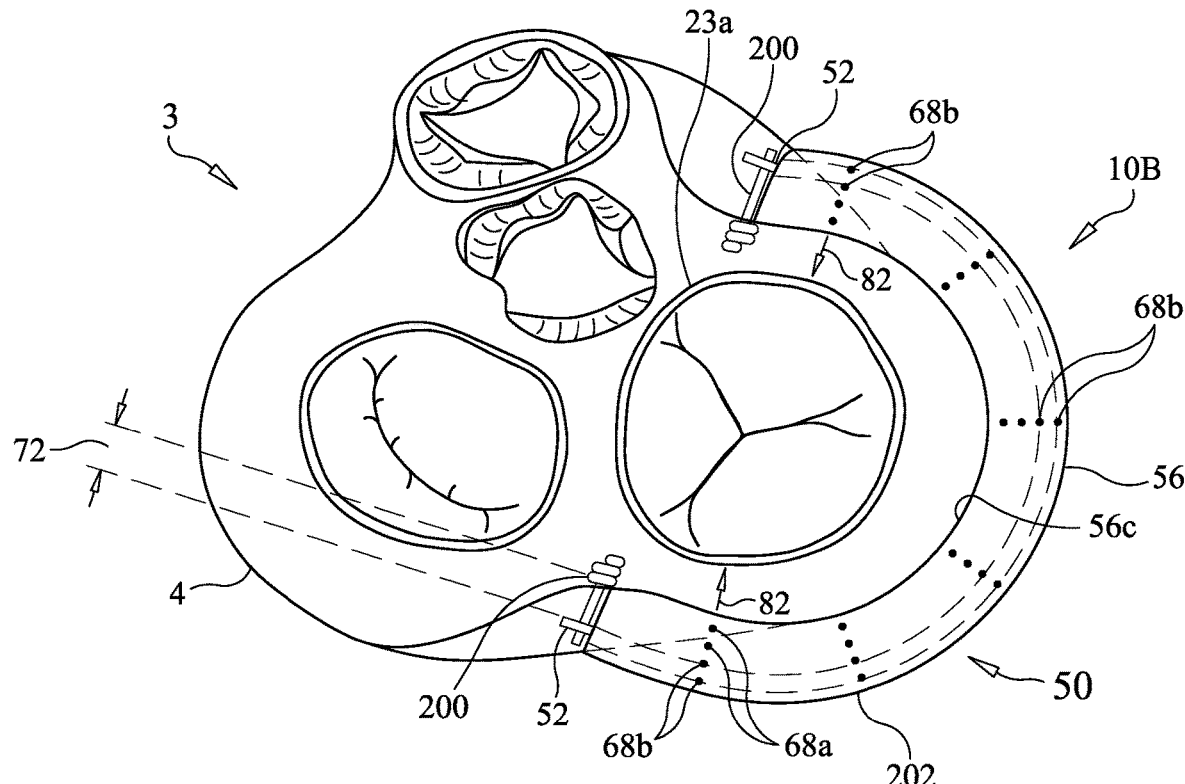
FIG. 17C illustrates the implanted device of FIG. 17B, after manual adjustment of the device.

FIG. 17C illustrates the implanted device 10B of FIG. 17B, after manual adjustment of the device to move rod/rib 202 relative to pad 56 so that rod/rib 202 is captured by stops 68b. After this adjustment the normal distance measurement between rod/rib 202 and the contact surface 56C is 72 and this greater distance (relative to distance 70) results in application of a force 82 that is greater than force 80 applied to the external wall of the heart 3, therefore resulting in greater deformation of the heart wall and annulus 23a of the mitral valve. Also, because the distance 72 is greater than 70 at both opposing locations 6A and 6P on the surfaces of the right ventricle 6 and because the distance between the rod portions at these locations does not change (due to the rigidity of the rod/rib 202) this results in the distance between the portions of the contact surface 56C at locations 6P and 6A being less than it was in FIG. 17B by an amount of 2(72−70) and therefore the tricuspid annulus 23 is deformed due to the deformation of the ventricular walls surrounding it. Similarly, the change in position of the rod/rib 202 relative to the contact surface 56C by repositioning the rod/rib 202 in the stops 68b at the intermediate locations cause an increase in force and deformation applied to the heart wall and tricuspid annulus apposite the intermediate locations. As illustrated in FIG. 17C this greater deformation/reshaping of the annulus 23a has resulted in the complete closing of the valve leaflets of the tricuspid valve 23 so that tricuspid valve regurgitation no longer occurs.

Figure 17D:
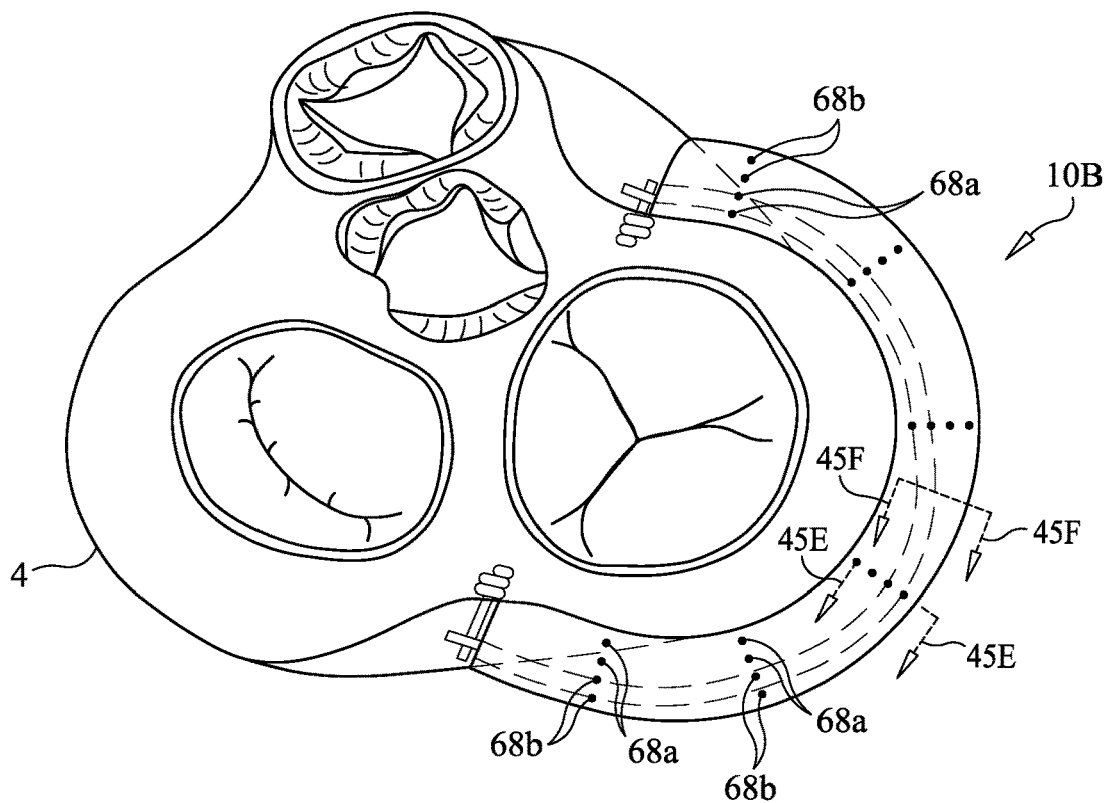
FIG. 17D shows only a posterior portion of a rod/rib of the device of FIG. 17B having been repositioned.

It is further noted that the device 10B is not limited to the amount of adjustment provided by the change in position of the rod/rib 202 from that shown in FIG. 17B to that shown in FIG. 17C and vice versa. Further variations in forces applied, and distances between opposing contact surfaces can be achieved by various partial adjustments of the rod/rib 202 relative to the stops 68a and 68b. That is, any individual portion of the rod/rib 202 can be adjusted from positioning within stops 68a to positioning within stops 68b, independently from the positioning of all other portions of the rod/rib 202 relative to its corresponding stops. As just one example, FIG. 17D shows only the posterior portion of the rod/rib 202 having been repositioned in the channel to be held by stops 68b, while the portions of the rod/rib 202 that apply forces at the anterior wall are positioned in the stops 68a in the channel, as are the portions of the rod/rib 202 intermediate of the posterior and anterior portions. In this instance, the reduction in distance between the contact surfaces 56C at 6P and 6A is only the difference between distance 72 and distance 70. However, in this instance, this was sufficient reduction to close the tricuspid valves and eliminate tricuspid valve regurgitation as illustrated in FIG. 17D. As noted, there are many other combinations of modification of relative positioning of the rod/rib in each of the sets of stops provided, so that the force profile about the tricuspid valve, to the extent that it is surrounded by the device 10B can be customized.

Figure 18:
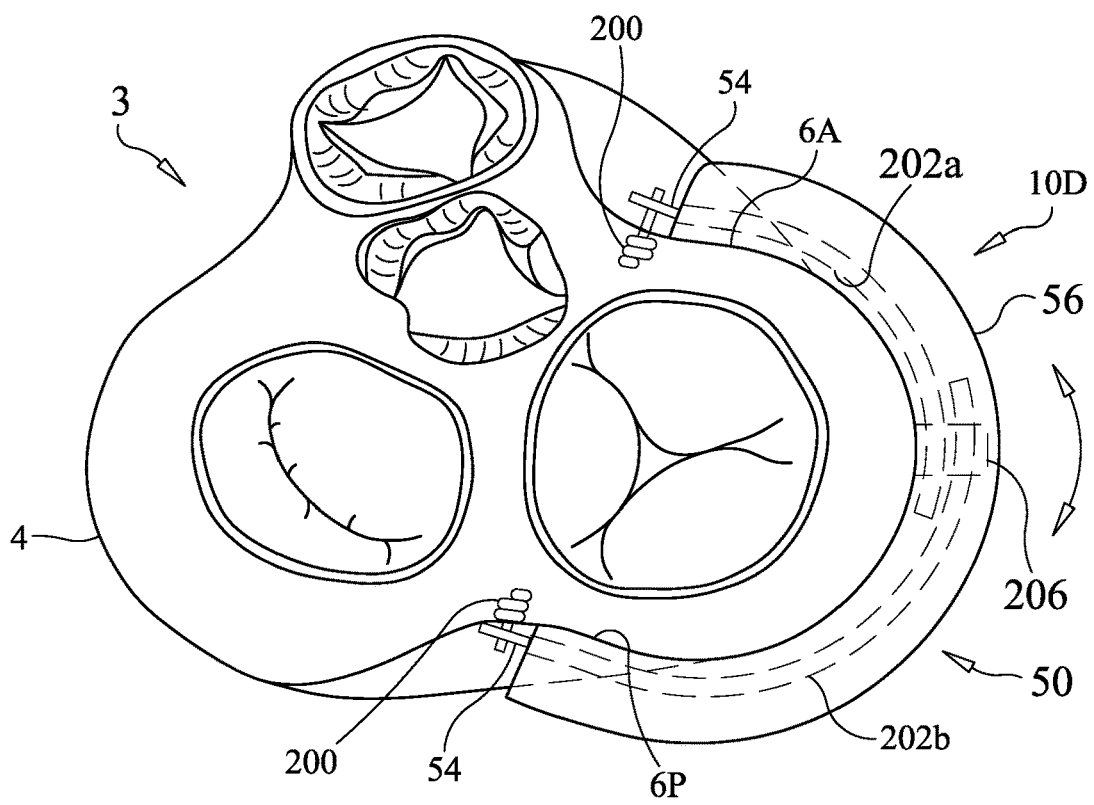
FIG. 18 illustrates a device having been installed epicardially on a heart of a patient for treatment of tricuspid valve regurgitation, according to an embodiment of the present invention.

FIG. 18 illustrates a device 10D having been installed epicardially on the heart 3 of a patient for treatment of tricuspid valve regurgitation according to an embodiment of the present invention. Like device 10B, a measurement between the anterior and posterior locations 6A and 6P of the right ventricle can optionally be made, during visualization of the tricuspid valve 23 to watch for regurgitation amounts occurring under various force and deformation levels, so as to identify an optimum distance between the contact surfaces 56c of the device that will be applied to the locations where the measurement was taken. Alternatively the device 10D can be installed without taking the preliminary measurement and the device 10D can then be adjusted under visualization to reduce and/or eliminate tricuspid valve regurgitation. This adjustment after implantation can be performed whether or not the preliminary measurement has been taken. As with the device 10B, the device 10D is attached epicardially, in or about the plane of the tricuspid valve 23, as illustrated in FIG. 18. FIG. 18 illustrates device 10D having been installed epicardially on the heart 3 of a patient for treatment of tricuspid valve regurgitation as one of the preferred embodiments of location of implantation. In this preferred embodiment, device 10D can be installed epicardially on the heart 3 over a target location to effect reshaping of the tricuspid valve annulus 23a. Preferably, the contact pad 56 of the device is as long as can be fitted to the heart 3 at this location, so that the contact surface 56C of the pad contacts the heart wall around as much of the tricuspid valve annulus 23a as possible. FIG. 18 shows that the pad 56 of the device 10D surrounds greater than 50% of the annulus 23a and can apply forces to three sides of the heart wall (anterior, posterior and lateral). Preferably the pad 56 extends as far as is physically possible before it is prevented by heart structures from extending any further. Thus, the pad may surround a percentage of the annulus in a range from 30% to 70%, preferably 40% to 70%, more preferably 50% to 70%, even more preferably 60% to 70%. Again it is noted that the epicardial approach allows patient specific treatment on the beating heart. The percentages are commonly used in open heart surgery where the patient's heart is stopped and the beating heart condition can only be approximated. In this epicardial approach the heart will be beating and patient specific geometry and treatment will drive the clinical benefit. The device 10D may be anchored to the wall of the heart 3 at the level of the tricuspid valve 23 via fixators 200 in a manner as described with regard to previous embodiments described.

Rod/rib 202 is provided in two parts, an first part 202a and a second part 202b that, extend through the main body 50 of device 10D and form extension rods 52 that extend from both ends of main body 50. Rod/rib portions 202a, 202b are preferably substantially curved as shown, with a curvature configured to conform to the curvature of the epicardial walls of the right atrium 6 at the level of the tricuspid valve 23 on the exposed epicardial sides. The main body is formed by pad 56 which surrounds or encases the portion of the rod/ribs 202a, 202b extending therethrough. As shown, the portions 202a, 202b are about equal in length, but this need not be the case. In FIG. 18, the portions 202a, 202b are joined together by an actuator 206, which may be a gearbox, one-way ratchet mechanism, or other mechanical component that allows the portions 202a, 202b to be driven therethrough in at least one direction. By driving the portions 202a, 202b through actuator 206, this effectively decreases or increases the distance between the contact surfaces 56C contacting the anterior and posterior walls 6A and 6P of the heart 3 on opposite sides of the tricuspid valve 23 as illustrated in FIG. 18. For example, by relatively driving the portions 202a, 202b so that 202b moves upward through the actuator 206 and/or 202a moves downward through the actuator 206 in FIG. 46, this causes the distance between contact at 6A and 6P to be reduced, thereby increasing the force and deformation on the walls of the heart 3 and on annulus 23a. Of course, movement in the opposite directions would have the opposite effect of reducing the force and decreasing the deformation. Actuator 206 may be manually adjustable, particularly in the directions for increasing the force/deformation, by manually forcing the ends of the device toward one another so that the described movement occurs. In the case of a one way ratchet mechanism, the mechanism would then prevent the ends from moving away from the new positions. Actuator 206 may be a motorized gearbox, with battery power, for example, which could be actuated either directly by an actuation switch on the device 10D, or preferably can be configured for remote wireless actuation. The motorized actuator 206 can be actuated to either increase or decrease the forces/deformation applied by the device 10D to the heart 3.

While the present invention has been described with reference to the specific embodiments thereof, it should be understood by those skilled in the art that various changes may be made and equivalents may be substituted without departing from the true spirit and scope of the invention. For example, the invention can be used in other target tissues or organs, such as other valves of the heart, pulmonary tissues, the gastrointestinal system (including, but not limited to the stomach, small intestine, and/or large intestine), renal system, urinary system or any other tissues/organs that may be effectively treated with direct mechanical manipulation.

In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. An epicardial device for reducing or preventing regurgitation of blood through a valve of a heart, said device comprising:
    a main body having a segment adapted to apply force to an epicardial surface of the heart;
    a member that applies counterforce to said force applied by said segment; and
    an adjustment mechanism that is mechanically operable to change the force applied by said segment;
    wherein said segment comprises a rigid structural rib contained within a pad;
    wherein said pad comprises a contact surface configured to apply said force to the epicardial surface;
    wherein said adjustment mechanism is operable to change a distance of said rigid structural rib from said contact surface; and
    wherein said adjustment mechanism can be mechanically operated before or after anchoring of said device to the epicardial surface wherein said anchoring of said device includes mechanical anchoring of said device against the heart surface, said adjustment mechanism thereby eliminating a need to remove said device and reinstall said device after being reconfigured, also eliminating a need to remove anchors prior to mechanically operating said adjustment mechanism.

2. The epicardial device of claim 1,
    wherein said adjustment mechanism comprises a channel having stops formed therein;
    wherein a first set of said stops maintains said rib at a first predetermined distance from said contact surface; and
    wherein a second set of said stops maintains said rib at a second predetermined distance from said contact surface, said second predetermined distance being unequal to said first predetermined distance.

3. The epicardial device of claim 2, wherein said device is manually operable to change a location of said rib from being held by said first set of stops to a location where said rib is held by said second set of stops, by manually pushing against said rib, via application of pressure to said body at locations apposite said first set of stops, while applying counter-pressure to said contact surface at locations that are not apposite to said first set of stops.

4. The epicardial device of claim 1 configured for reshaping an annulus of a mitral valve of the heart.

5. The epicardial device of claim 1 configured for reshaping an annulus of a tricuspid valve of the heart.

6. The epicardial device of claim 1, wherein said valve is the mitral valve and said epicardial device is configured for reshaping an annulus of the mitral valve of the heart;
    said main body comprises an anterior segment adapted to be contacted to an anterior surface of the heart and comprising said member, a posterior segment adapted to be contacted to a posterior surface of the heart and comprising said segment and a lateral segment joining said anterior segment and said posterior segment;
    wherein said posterior segment comprises said segment adapted to apply force and said anterior segment comprises said member that applies counterforce to said force.

7. The epicardial device of claim 6, wherein the annulus of the mitral valve lies in a plane between the left atrium and the left ventricle of the heart, the anatomy of the heart includes an aorta, a pulmonary trunk, a superior vena cava, a transverse sinus, an oblique sinus, and an atrioventricular groove;
    wherein said anterior segment is configured to be positioned in the transverse sinus of the heart by ending at the right atrium;
    wherein said posterior segment is configured to be positioned on or inferior to the atrioventricular groove of the heart and ending at the right ventricle; and
    wherein said lateral segment extends between said anterior segment and said posterior segment.

8. The epicardial device of claim 7, wherein said posterior segment is curved to follow a contour of a posterior surface of the heart.

9. The epicardial device of claim 7, wherein said anterior segment is substantially straight.

10. The epicardial device of claim 1, wherein said member that applies counterforce comprises first and second tissue anchors, said first tissue anchor adapted to anchor a first end portion of said device to the heart and said second tissue anchor adapted to anchor a second end portion of said device to the heart, wherein said segment is located between said first and second end portions.

11. The epicardial device of claim 1,
wherein said main body comprises an anterior segment adapted to be contacted to an anterior surface of the heart, a posterior segment adapted to be contacted to a posterior surface of the heart and a lateral segment joining said anterior segment and said posterior segment;
wherein said posterior segment comprises said segment adapted to apply force and said anterior segment comprises said member that applies counterforce to said force.

12. The epicardial device of claim 11, further comprising an inferior segment extending from said main body in a direction transverse to a direction in which said anterior, lateral and posterior segments extend.

13. The epicardial device of claim 12, wherein said inferior segment comprises a second segment adapted to apply a second force to an epicardial surface of the heart;
wherein said inferior segment comprises an adjuster that is manually operable to change the second force applied by said second segment; and
wherein said adjuster can be manually operated before or after anchoring of said inferior segment to the epicardial surface.

14. The epicardial device of claim 1,
wherein said pad is covered by a sheath.

15. The epicardial device of claim 14, further comprising a flap extending from said pad, wherein said flap is configured for receiving tissue anchors therethrough to anchor said epicardial device to the heart.

16. The epicardial device of claim 15, wherein said flap is an extension of said sheath.

17. A method of epicardial treatment of mitral valve regurgitation associated with the mitral valve of a heart, the anatomy of the heart including an aorta, a pulmonary trunk, a superior vena cava, a transverse sinus, a left atrial appendage, and an oblique sinus, the method comprising:
providing a device having an anterior segment, an anterior end, a posterior segment, a posterior end and a lateral segment extending between the anterior segment and the posterior segment;
positioning the anterior and posterior segments epicardially on the heart at locations apposite to an annulus of the mitral valve, such that the anterior and posterior segments apply force sufficient to reshape the annulus;
visually observing whether the mitral valve regurgitation has been successfully reduced or eliminated; and
when it is observed that the mitral valve regurgitation has not been successfully reduced or eliminated, adjusting the force applied by the anterior and posterior segments, while the anterior and posterior segments remain positioned epicardially on the heart at locations apposite to the annulus of the mitral valve, by manually operating an adjuster that changes a distance between a contact surface of the posterior or anterior segment and a structural rib portion of the posterior or anterior segment, respectively.

18. The method of claim 17, wherein said adjusting is performed prior to anchoring the device epicardially on the heart.

19. The method of claim 17, wherein said adjusting is performed after anchoring the device epicardially on the heart.

20. The method of claim 17, wherein said adjusting comprises applying pressure to the structural rib portion within a pad of the posterior or anterior segment, at locations apposite a first set of stops within a channel in said pad, while applying counter-pressure to a contact surface of the pad at locations that are not apposite to said first set of stops, thereby driving the rib from a first set of stops to a second set of stops;
wherein said first set of stops are located at a first depth from said contact surface within said channel and said second set of stops are located at a second depth from said contact surface within said channel, said first depth being unequal to said second depth.

21. The method of claim 20, wherein said posterior segment comprises the pad.

22. The method of claim 17, wherein said adjusting comprises mounting a shim on or removing a shim from a first contact surface of a pad of said anterior or posterior segment; where the shim comprises a second contact surface;
wherein, when said shim has been mounted over said first contact surface, said second contact surface is configured to apply said force as a second force greater than said first force; and
wherein the change of distance comprises the change in distance between the second contact surface and the structural rib portion versus the distance between the first contact surface and the structural rib portion.

23. The method of claim 22, wherein said posterior segment comprises the pad.

24. The method of claim 17, wherein said visually observing is performed echocardiographically.

25. The method of claim 17, further comprising:
prior to said positioning, applying a force to a posterior surface of the heart while visually observing blood flow through the mitral valve;
varying the force to establish a force that successfully reduces or eliminates the mitral valve regurgitation; and
measuring a distance between a posterior external wall and an anterior external wall of the heart in a deformed state resultant from the application of force that successfully reduces or eliminates the mitral valve regurgitation, the distance being measured between locations where the device is to be positioned; and
wherein said providing a device includes selecting the device to have a distance between said anterior and posterior segments that corresponds to the distance measured.

26. The method of claim 17, wherein said positioning comprises:
positioning the anterior segment in the transverse sinus of the heart;
positioning the posterior segment on or inferior to the atrioventricular groove of the heart, wherein the device reshapes the annulus of the mitral valve; and wherein said anterior and posterior ends are spaced apart from one another by a predetermined distance and remain separated by a gap or opening after said positionings.

27. An epicardial device for reducing or preventing regurgitation of blood through a valve of a heart, said device comprising:
a main body having a segment adapted to apply force to an epicardial surface of the heart;
a member that applies counterforce to said force applied by said segment; and
an adjuster that is manually operable to change the force applied by said segment;

wherein said adjuster can be manually operated before or after anchoring of said device to the epicardial surface;

wherein said segment comprises a rigid structural rib contained within a pad;

wherein said pad comprises a contact surface configured to apply said force to the epicardial surface;

wherein said adjuster comprises a channel having stops formed therein;

wherein a first set of said stops maintains said rib at a first predetermined distance from said contact surface; and wherein a second set of said stops maintains said rib at a second predetermined distance from said contact surface, said second predetermined distance being unequal to said first predetermined distance.

28. The epicardial device of claim 27, further comprising securement features configured to secure said shim to said first contact surface;

wherein, when said shim has been secured to said first contact surface, said second contact surface is configured to apply said force as a second force greater than said first force.

29. An epicardial device for reducing or preventing regurgitation of blood through a valve of a heart, said device comprising:

a main body having a segment adapted to apply force to an epicardial surface of the heart;

a member that applies counterforce to said force applied by said segment; and an adjuster that is manually operable to change the force applied by said segment;

wherein said adjuster can be manually operated before or after anchoring of said device to the epicardial surface;

wherein said segment comprises a first contact surface configured to apply said force as a first force to the epicardial surface;

wherein said adjuster comprises a shim configured to be aligned with said first contact surface, said shim having a second contact surface.

* * * * *